United States Patent [19]

Kusunoki et al.

[11] Patent Number: 5,529,580
[45] Date of Patent: Jun. 25, 1996

[54] SURGICAL RESECTING TOOL

[75] Inventors: Hiroyuki Kusunoki, Higashimurayama; Koji Shimomura, Hachioji; Takeshi Yokoi, Hachioji; Shozo Shibuya, Hachioji; Mototsugu Ogawa, Hachioji; Takeaki Nakamura, Hino; Tadao Hagino, Yokohama, all of Japan

[73] Assignee: Olympus Optical Co., Ltd., Tokyo, Japan

[21] Appl. No.: 237,832

[22] Filed: May 4, 1994

Related U.S. Application Data

[63] Continuation of Ser. No. 986,874, Dec. 4, 1992, abandoned, which is a continuation of Ser. No. 773,786, Oct. 11, 1991, abandoned, which is a continuation of Ser. No. 471,752, Jan. 29, 1990, abandoned, which is a continuation-in-part of Ser. No. 230,944, Aug. 11, 1988, abandoned.

[30] Foreign Application Priority Data

| Oct. 30, 1987 | [JP] | Japan | 62-277046 |
| Dec. 1, 1987 | [JP] | Japan | 62-305382 |
| Dec. 2, 1987 | [JP] | Japan | 62-184286 |
| Dec. 2, 1987 | [JP] | Japan | 62-305435 |
| Dec. 2, 1987 | [JP] | Japan | 62-305437 |

[51] Int. Cl.$^6$ ............................................. A61B 17/32
[52] U.S. Cl. ............................ 606/170; 606/180; 604/22
[58] Field of Search ................................. 606/167, 180, 606/170, 171; 604/22

[56] References Cited

U.S. PATENT DOCUMENTS

| 4,512,344 | 4/1985 | Barber . |
| 4,646,738 | 3/1987 | Trott . |
| 4,729,763 | 3/1988 | Henrie ..................... 606/170 |

FOREIGN PATENT DOCUMENTS

| 2848314C2 | 12/1982 | Germany . |
| 3447681A1 | 7/1985 | Germany . |
| 265133 | 11/1986 | Japan . |

*Primary Examiner*—Michael H. Thaler
*Attorney, Agent, or Firm*—Armstrong, Westerman, Hattori, McLeland & Naughton

[57] ABSTRACT

A surgical resecting tool (1) whereby a cartilage, cartilage knob or tumor within a body cavity, for example, such articulation cavity as of a knee is resected from outside the body cavity without being incised and is taken out of the body cavity is provided with a rigid outer tube (4) removably provided in the front part of a body part (2) which is also a holding part and has a rotary power source 28. The outer tube (4) is provided with an opening (7) near the front end part and with a curved part 9 in the rear of the opening (7). The outer tube 4 is provided with a cutting part (13) in the front end part and is removably connected in the rear end part to the rotary power source (28) to resect a living body tissue by rotating and driving the cutting part (13). An inner tube (6) having a flexible part (12) at least in the position corresponding to the above mentioned curved part (9) is inserted through the outer tube (4).

10 Claims, 19 Drawing Sheets

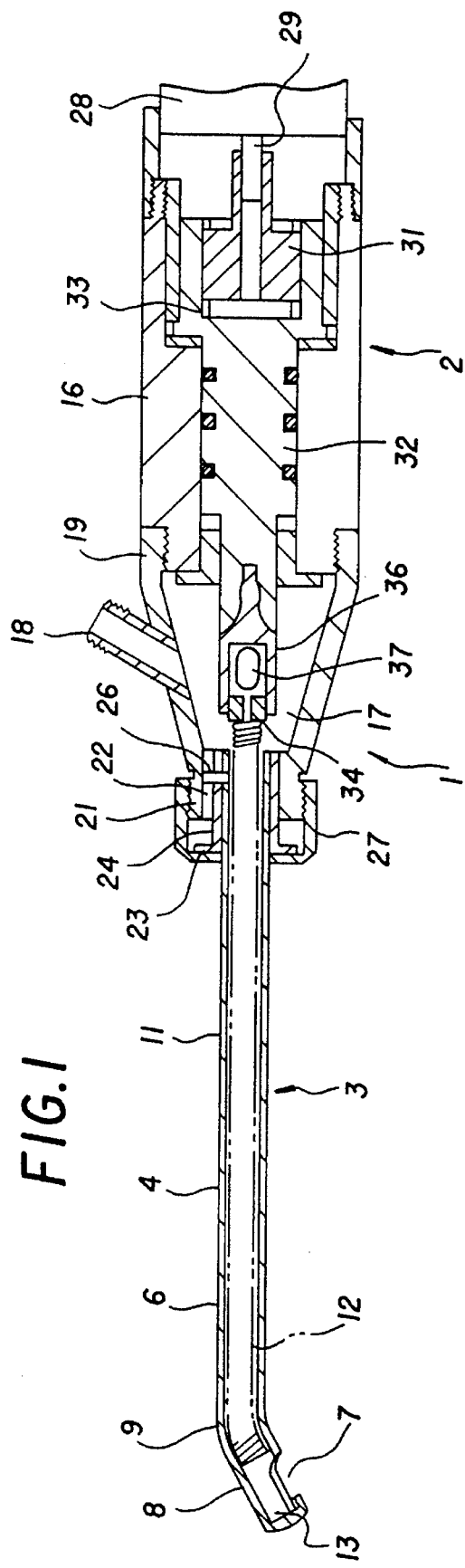
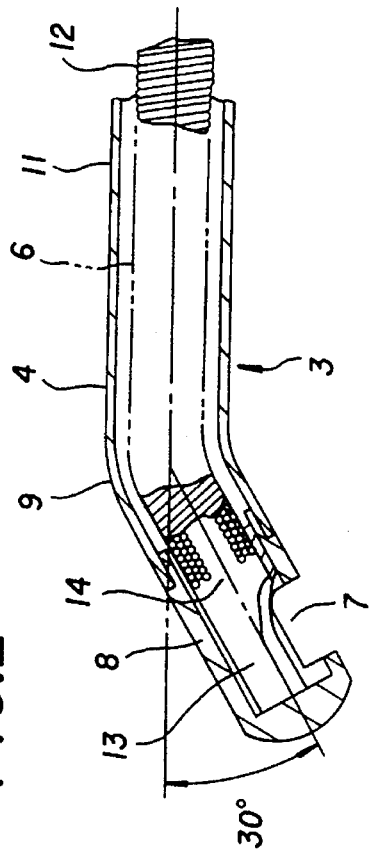
FIG.1
FIG.2

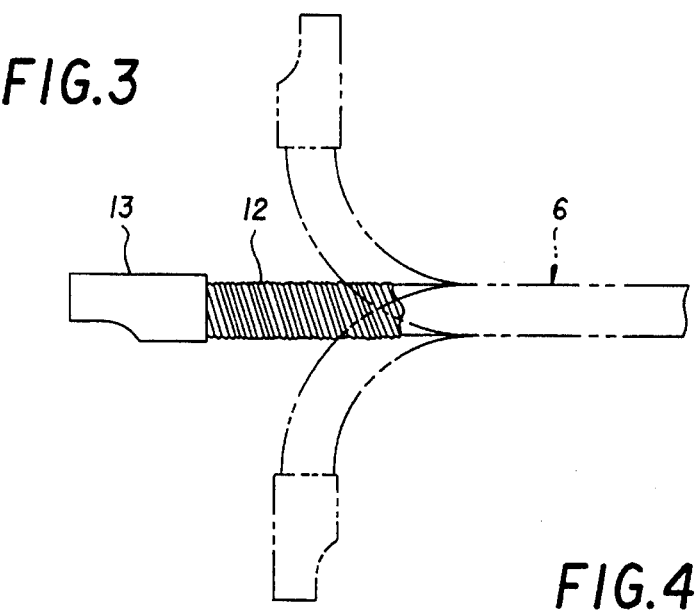
FIG.3
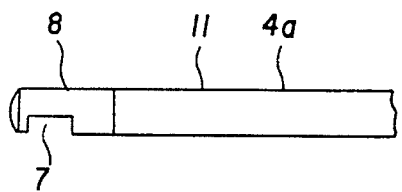
FIG.4(a)
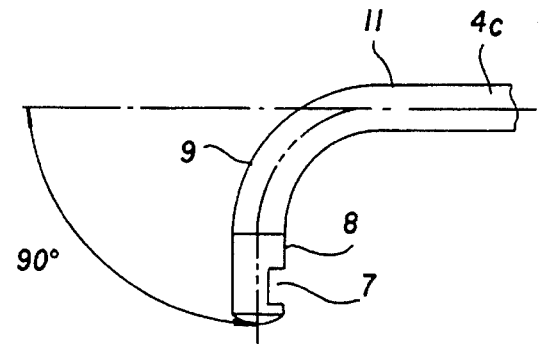
FIG.4(c)
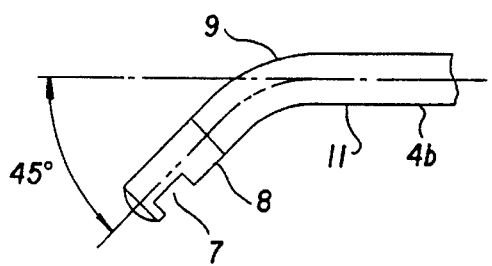
FIG.4(b)
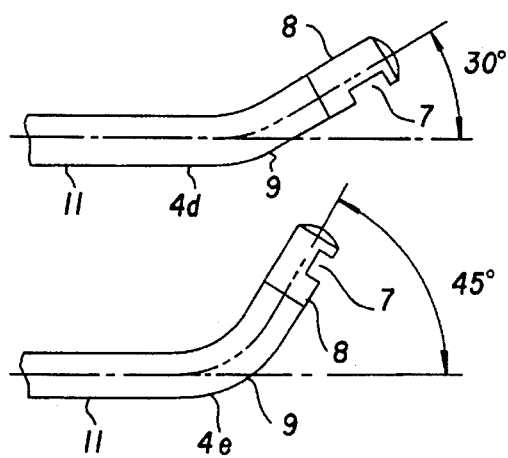
FIG.4(d)
FIG.4(e)

FIG.5
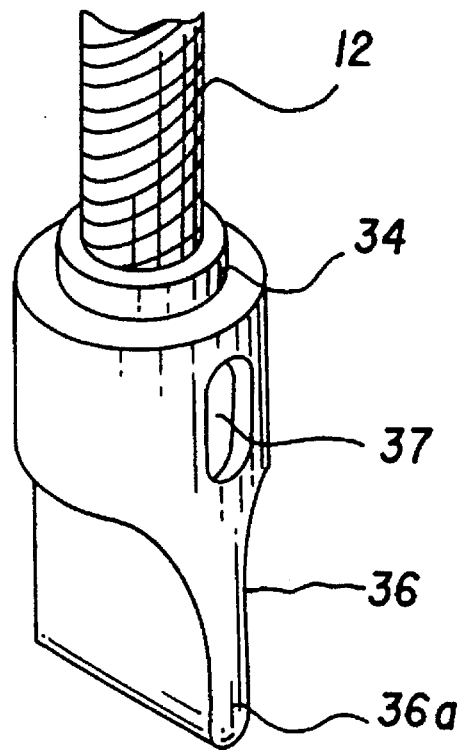
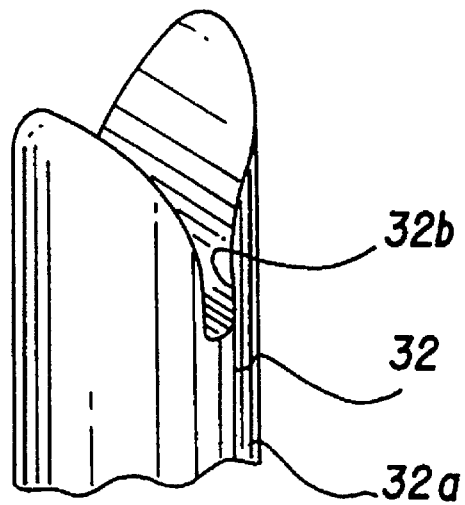

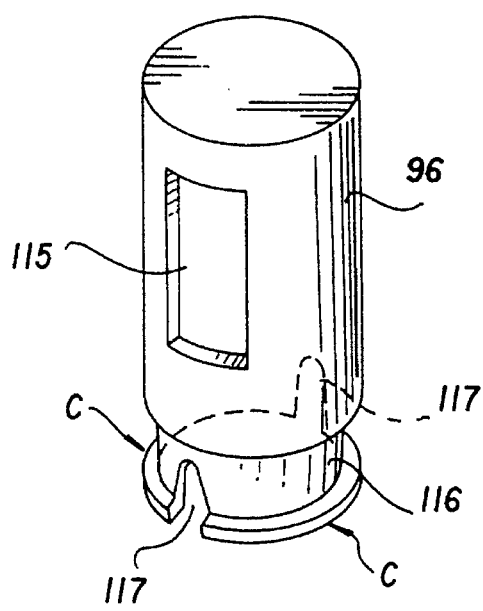
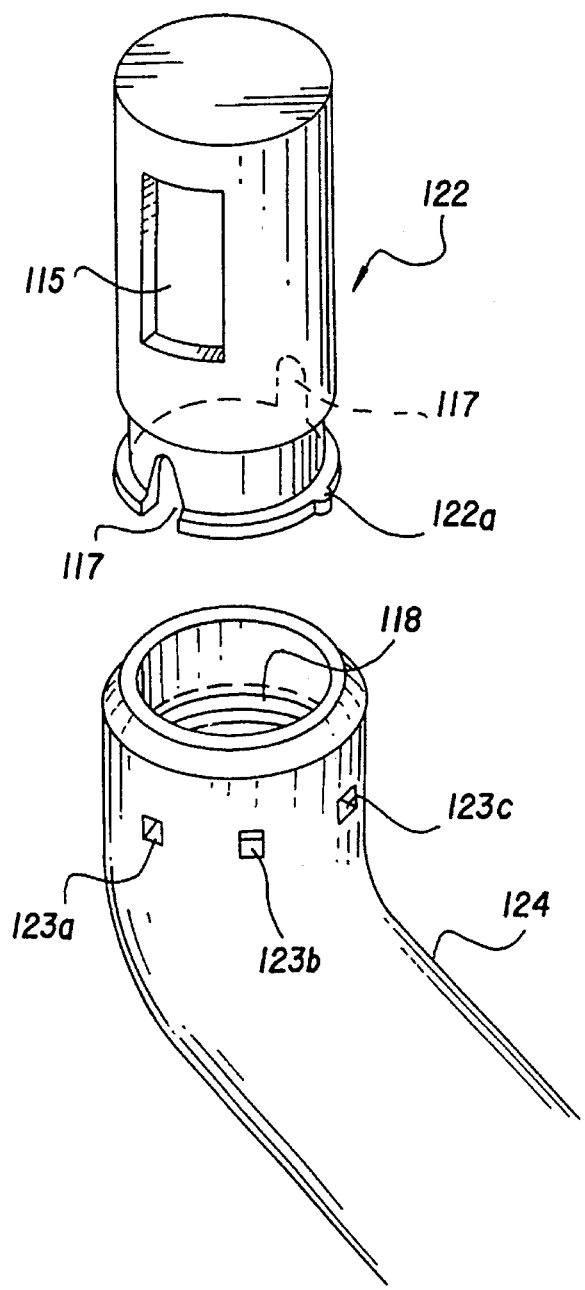
FIG.15
FIG.16

FIG.17
FIG.18
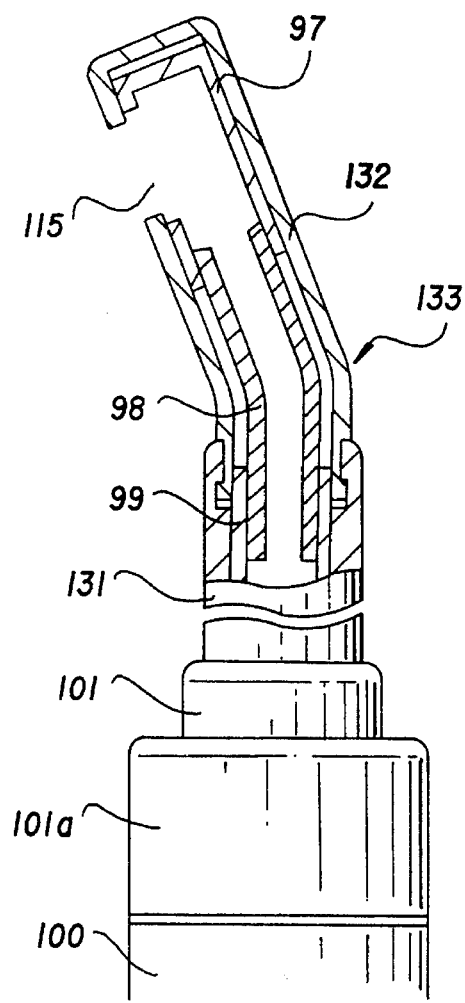
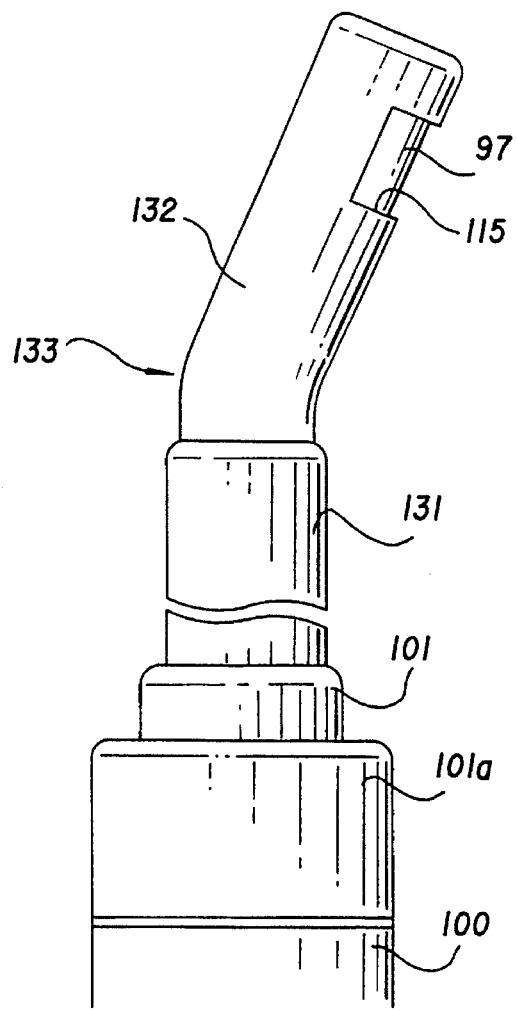

FIG.19
FIG.20
FIG.21
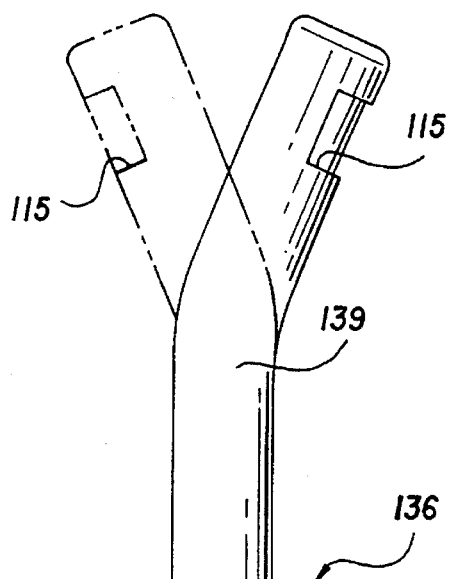
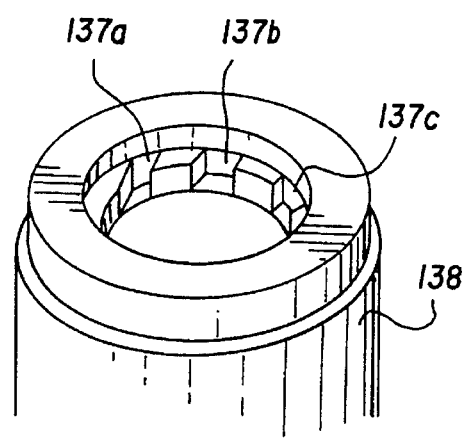
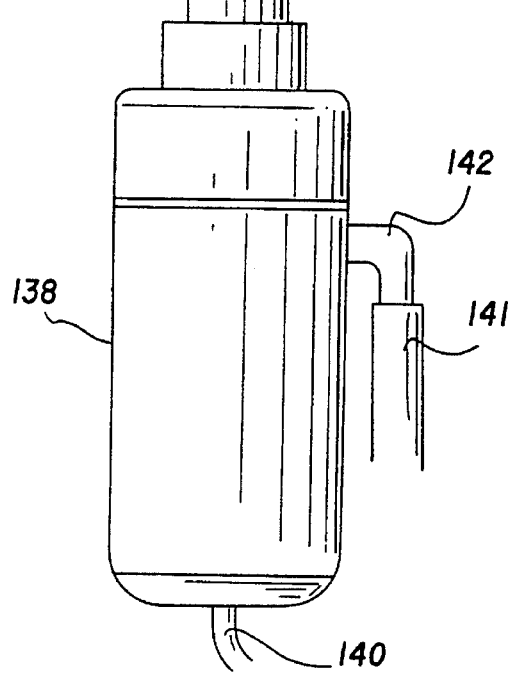
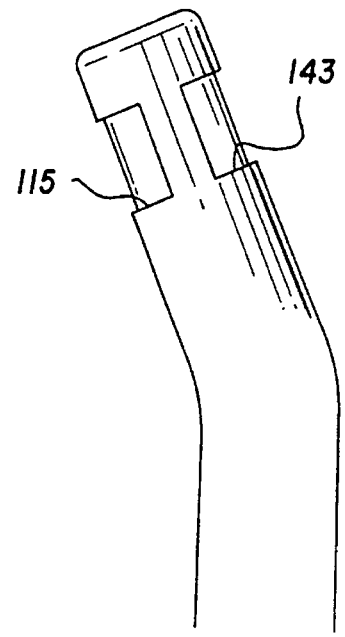

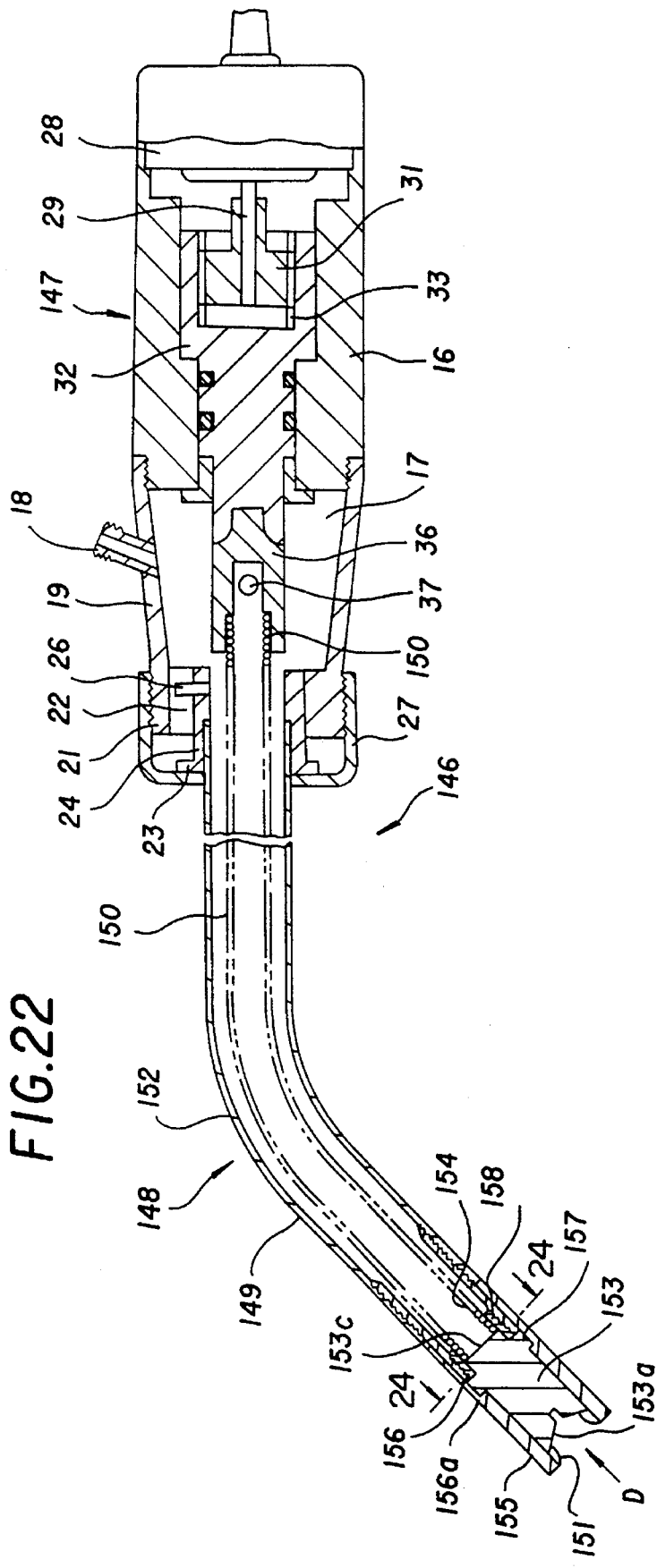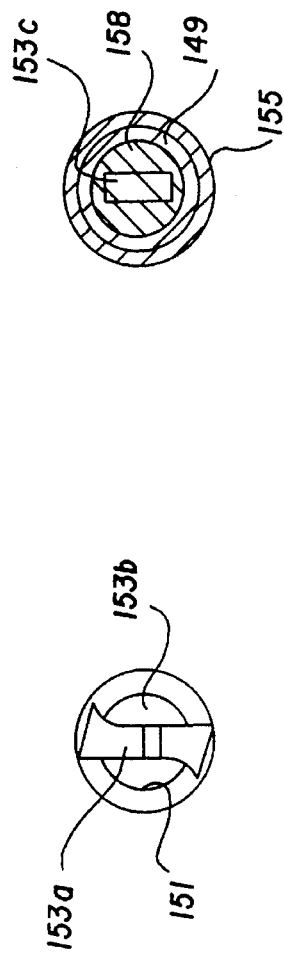

FIG.41(a)
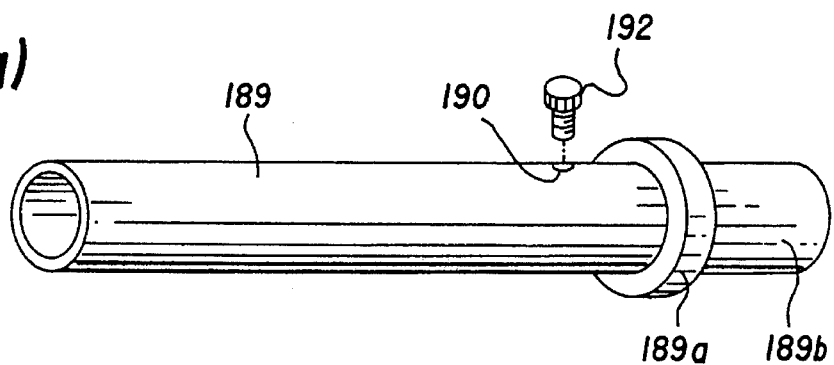
FIG.41(b)
FIG.41(c)
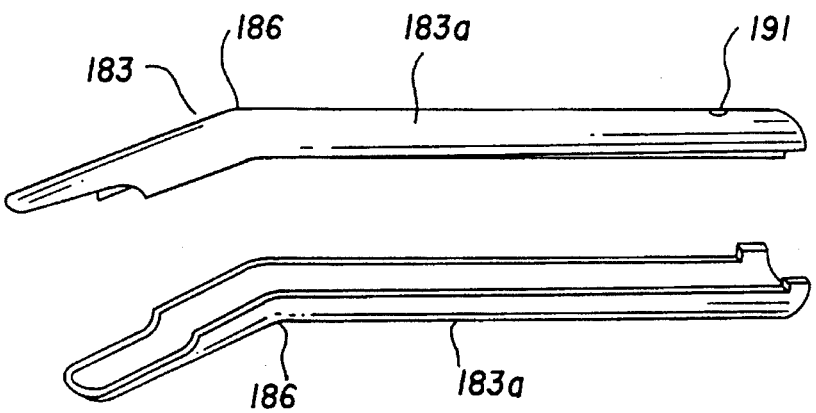
FIG.41(d)
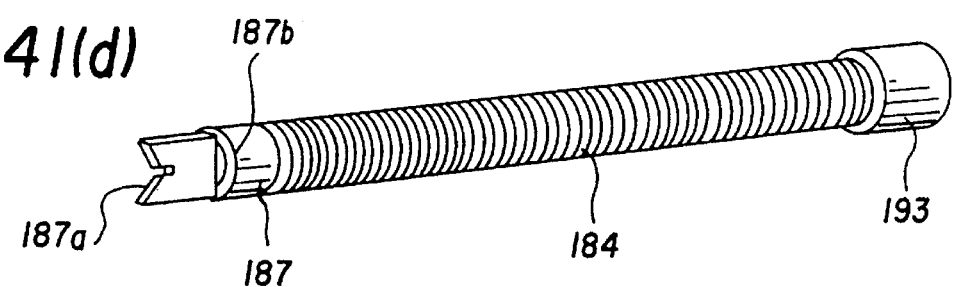

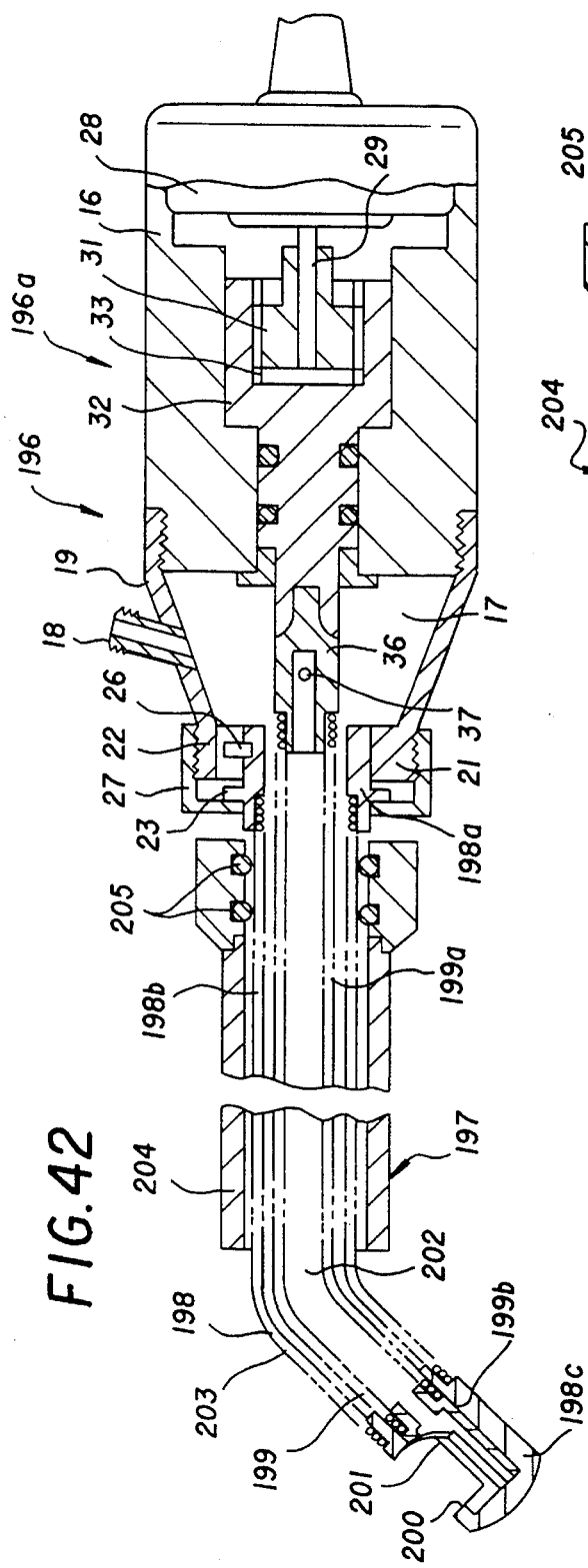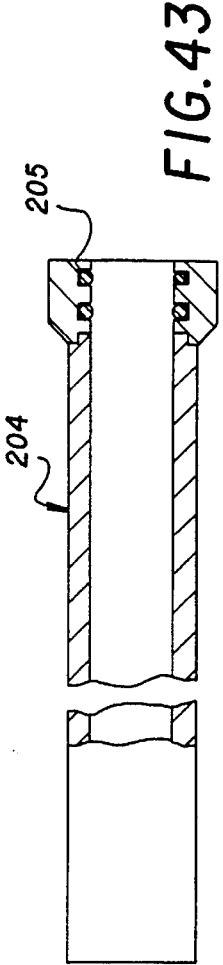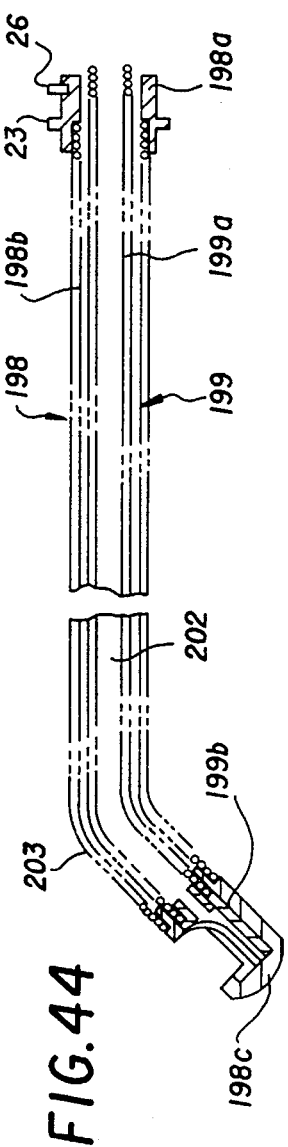
FIG.42
FIG.43
FIG.44

FIG.45
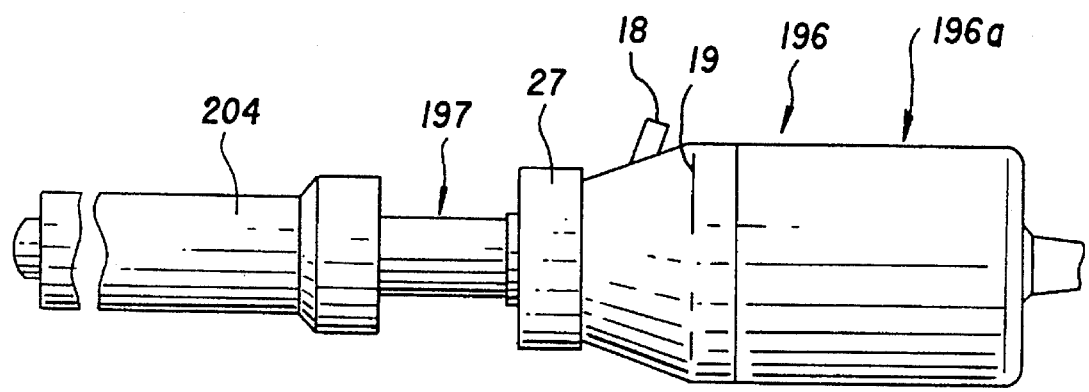
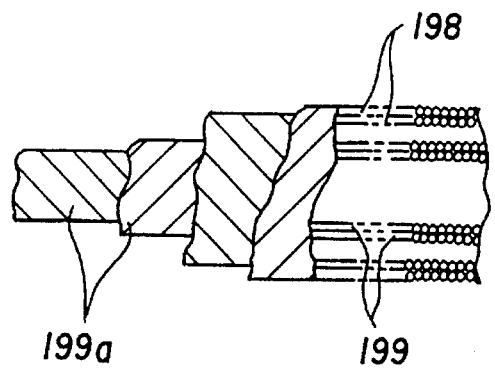
FIG.46

SURGICAL RESECTING TOOL

This application is a continuation of application Ser. No. 986,874, filed on Dec. 4, 1992, now abandoned, which was a continuation of application Ser. No. 773,786 filed on Oct. 11, 1991, now abandoned, which was a continuation of application Ser. No. 471,752, filed on Jan. 29, 1990, now abandoned which was a continuation-in-part application of application Ser. No. 230,944 filed on Aug. 11, 1988.

FIELD OF THE INVENTION

This invention relate to a surgical resecting tool whereby a cartilage (articulation meniscus or articulation cartilage), cartilage knob or tumor within a body cavity, for example, such articulation cavity as of a knee is resected from outside the body cavity without being incised and is taken out of the body cavity.

BACKGROUND OF THE INVENTION

An articulation has been conventionally operated on mostly by an incising method (open surgery). For example, in a general operation on an articulation, a tumor on a kneepan is resected or a broken cartilage or bone is resected. However, such operation has required a comparatively large incision. Therefore, there have been defects that an external injury has been produced, a pain and motion limitation have followed and a long time has been required until the injury is perfectly cured.

Therefore, there has been recently suggested a surgical resecting tool whereby a small pierced hole is formed in an articulation and an insertable part is inserted through this pierced hole to operate on the articulation without incising the articulation under the observation with an articulatoscope (endoscope). For example, in the publication of a Japanese patent application laid open No. 170449/1986, there is disclosed a surgical resecting tool having an insertable part in which a straight extending rigid inner tube provided in the tip part with a cutting part is inserted through a straight extending rigid outer tube. However, with this straight extending rigid insertable part, there has been a problem that, in the case of a resection within an articulation cavity, there will be a part which can not be resected. In order to cope with this problem, a surgical resecting tool wherein an outer tube forming an insertable part is semi-rigid and has a bending habit is disclosed in a U.S. Pat. No. 4,646,738. However, in this prior art example, the insertable part is used as bent on the tip side to be in any form. There are problems that, when the insertable part contacts such hard tissue as a bone while being inserted, for example, into an articulation cavity, it will vary in the bending form to be hard to insert and, in some case, will not be able to reach a part to be resected.

Also, in this technique, there are problems that, when the outer tube is fixed as bent, it will be able to be assembled but the inner tube will not be able to be pulled out and the outer tube and inner tube will not be able to be well washed and will be unclean.

OBJECT AND SUMMARY OF THE INVENTION

An object of the present invention is to provide a surgical resecting tool which can be positively and easily inserted in the cutting part even into a part to be resected in a complicated deep part of such hard tissue as a bone and is easy in the resecting operation, simple in the formation and low in the cost.

In the surgical resecting tool of the present invention, an inner tube is provided with a flexible part at least in a part, an outer tube is provided with a curved part in the part corresponding to this flexible part and the above mentioned inner tube and outer tube are removably fitted to the body part. That is to say, the inner tube is made curvable, is inserted into the curved outer tube and is curved in any desired direction to be used for the resection.

Further, when any of a plurality of outer tubes different in the curved angle and curved direction is selected and fitted, the insertable part will be able to be inserted in the cutting part into any part.

The other features and advantages of the present invention will become apparent with the following explanation.

BRIEF DESCRIPTION OF THE DRAWINGS

FIGS. 1 to 6 relate to the first embodiment of the present invention.

FIG. 1 is an explanatory view of the formation of a surgical resecting tool.

FIG. 2 is an explanatory view of the formation of the tip part of an insertable part.

FIG. 3 is an explanatory view of an inner tube as curved.

FIG. 4 is an explanatory view of an outer tube.

FIG. 5 is an explanatory view showing a flexible shaft as connected.

FIG. 6 is an explanatory view of a surgical resecting tool as being used.

FIG. 7 is a schematic explanatory view of the formation of a surgical resecting tool.

FIG. 8 is an explanatory view of the formation of the tip part of an insertable part.

FIG. 9 is an explanatory view of an outer tube.

FIGS. 12 to 15 relate to a surgical resecting tool wherein a cutting part can be rotated.

FIG. 12 is a vertically sectioned view for explaining the structure of a surgical resecting tool.

FIG. 13 is a sectioned view in the direction of the arrows 13—13 in FIG. 12.

FIG. 14 is a sectioned view in the direction of the arrows 14—14 in FIG. 12.

FIG. 15 is an explanatory view showing the form of a movable outer tube part.

FIG. 16 is an explanatory view of the formation of a movable outer tube having a projection.

FIGS. 17 and 18 relate to the explanation of the formation of a movable outer tube having a bent part.

FIG. 17 is an explanatory view of the formation of a movable outer tube.

FIG. 18 is an explanatory view of a movable outer tube as rotated.

FIGS. 19 and 20 relate to a surgical resecting tool in which a movable outer tube part and an outer tube are made integral.

3

FIG. 19 is an explanatory view of an outer tube.

FIG. 20 is an explanatory view of a recess for connecting an outer tube.

FIG. 21 is an explanatory view of an outer tube having plurality of apertures.

FIGS. 22 to 26 are explanatory views of the formation of a surgical resecting tool wherein a cutting blade member provided at the tip of an inner tube,is removably fitted.

FIG. 22 is a sectioned view.

FIG. 23 is a view as seen in the direction indicated by the arrow D in FIG. 22.

FIG. 24 is a sectioned view in the direction of the arows 24—24 in FIG. 22.

Figure 25:
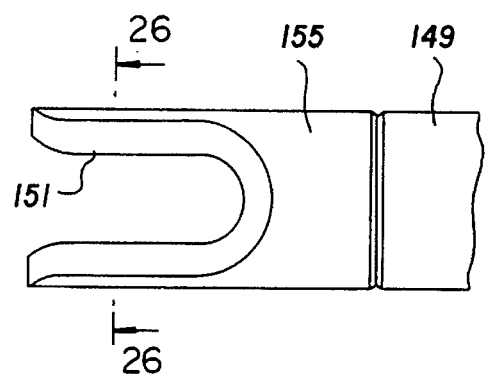

FIG. 25 is a side view showing the tip part of an outer tube.

Figure 26:
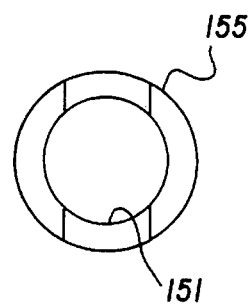

FIG. 26 is a sectioned view in the direction of the arrows 26—26 in FIG. 25.

Figure 27:
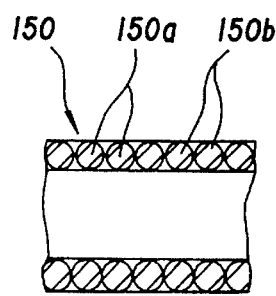

FIG. 27 is an explanatory view of a coil forming an inner tube filled in the gaps with a synthetic resin.

Figure 28:
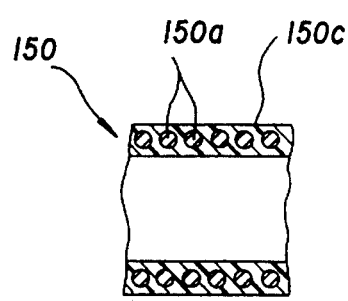

FIG. 28 is an explanatory view of a coil forming an inner tube embedded within a synthetic resin.

Figure 29:
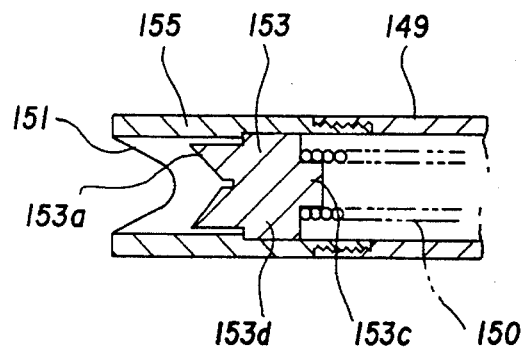

FIG. 29 is an explanatory view of a cutting blade formed of ceramics.

Figure 30:
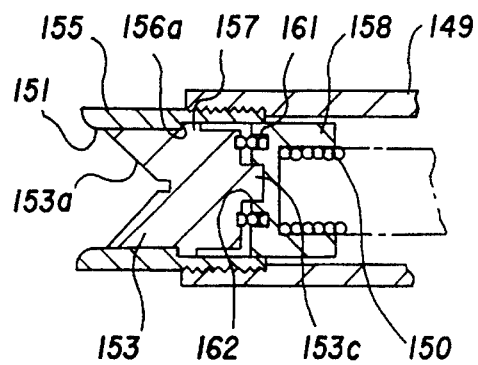

FIGS. 30 is an explanatory view of a cutting blade member having a cushioning member.

Figure 31:
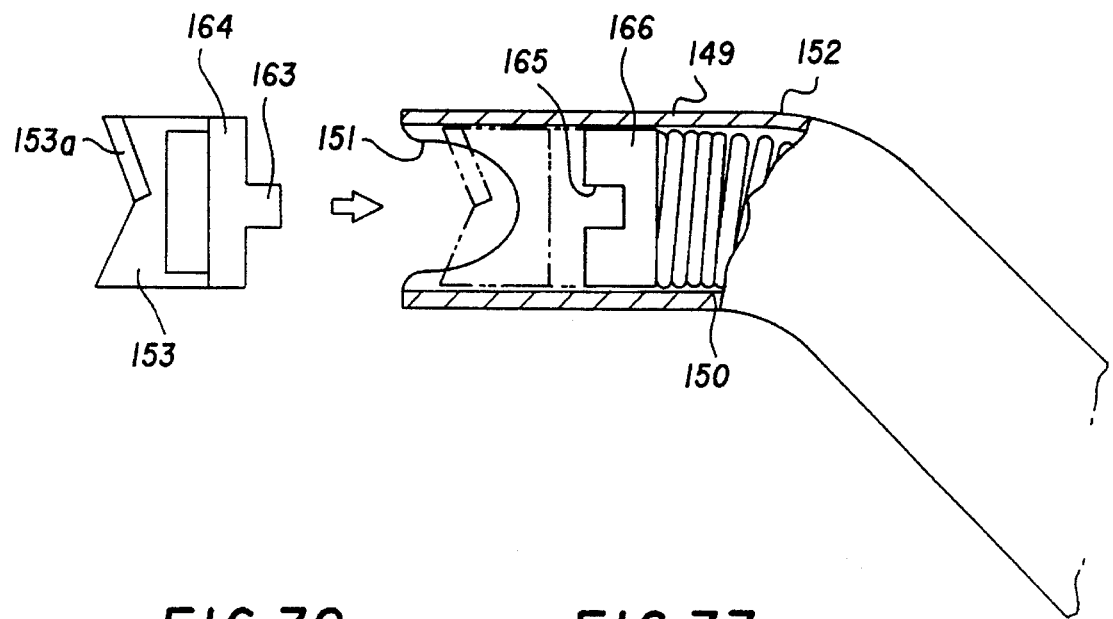
Figure 32:
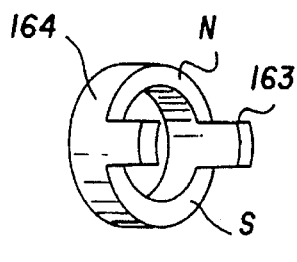
Figure 33:
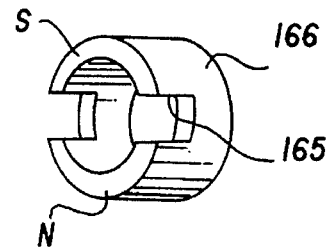

FIGS. 31 to 33 relate to explanatory views of a surgical resecting tool having a removably fitted cutting blade member.

FIG. 31 is an explanatory view of an insertable part tip as the cutting blade member is removed.

FIG. 32 is a perspective view of a magnet fixed to the cutting blade member.

FIG. 33 is a perspective view showing a magnet fixed to the tip of an inner tube.

Figure 34:
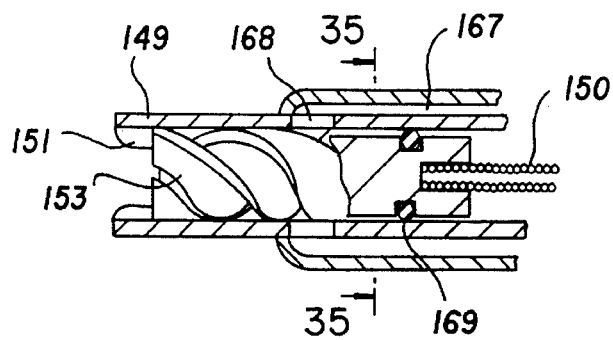
Figure 35:
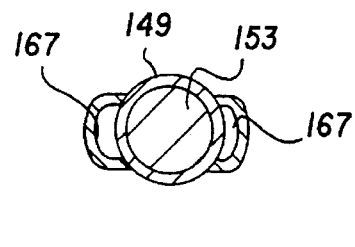

FIGS. 34 and 35 relate to a surgical resecting tool having an inner tube having suction paths on the outer periphery.

FIG. 34 is an explanatory view of the formation of the tip of an insertable part.

FIG. 35 is a sectioned view in the direction of the arrows 35—35 in FIG. 34.

Figure 36:
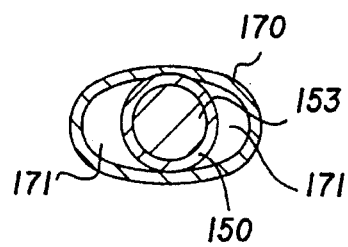

FIG. 36 is an explanatory view of an appearance, having an elliptic cross-section of a modification of FIGS. 34 and 35.

Figure 37:
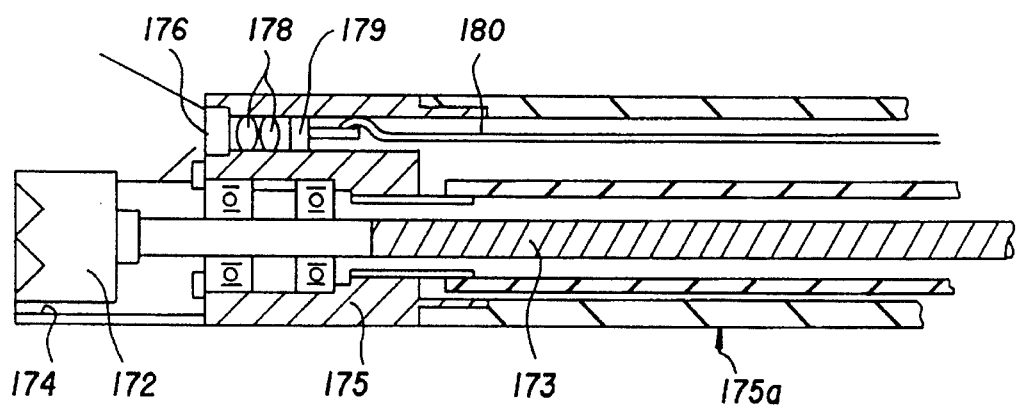

FIG. 37 is an explanatory view of the formation of an insertable part.

Figures 39, 40:
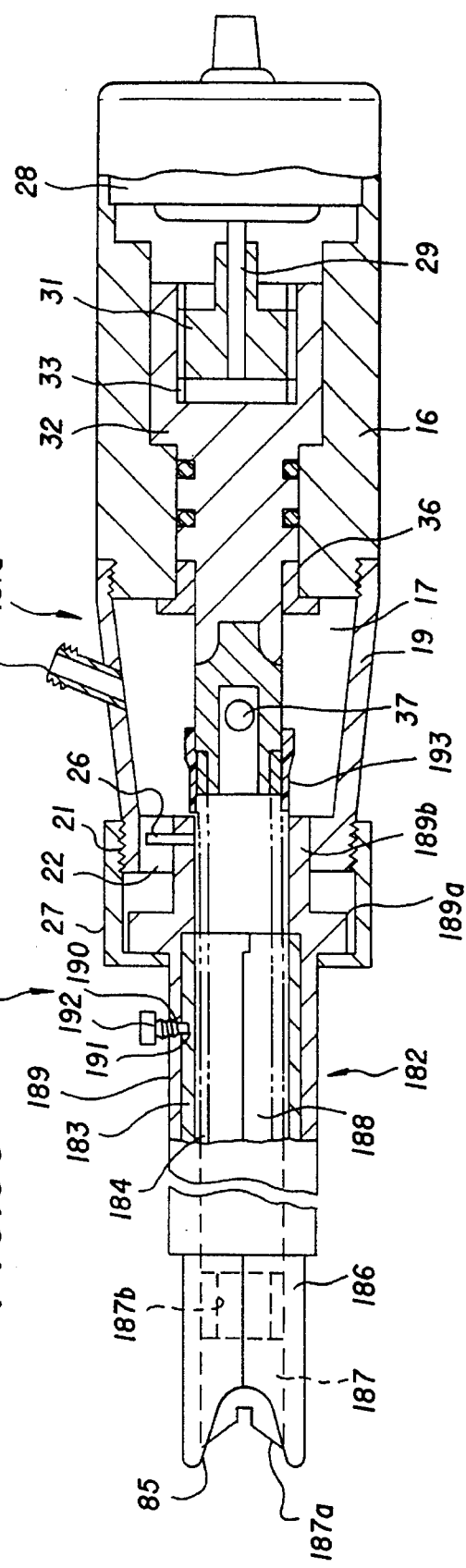

FIG. 39 to 41 relate to a surgical resecting tool having a dividable outer tube.

FIG. 39 is a sectioned view for explaining the formation of a surgical resecting tool.

FIG. 40 is an explanatory view of an outer tube.

FIG. 41 is a perspective view of an insertable part as disassembled.

FIGS. 42 to 45 relate to a surgical resecting tool provided in the inner rube with a curving habit part.

FIG. 42 is a sectioned view for explaining the formation of a surgical resecting tool.

FIG. 43 is an explanatory view of a guide pipe.

FIG. 44 is a sectioned view of an insertable part.

FIG. 45 is a general appearance view.

FIG. 46 is an explanatory view of the formation of a flexible tube.

Figure 47:
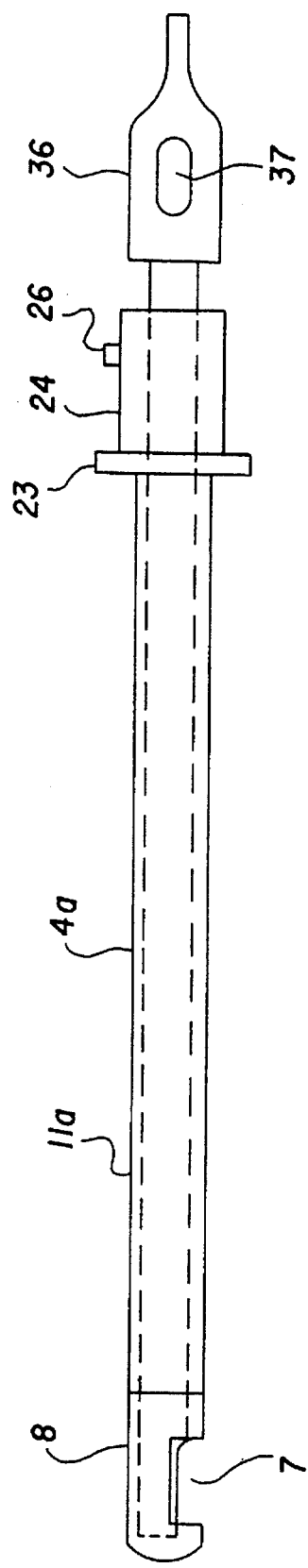
Figure 48:
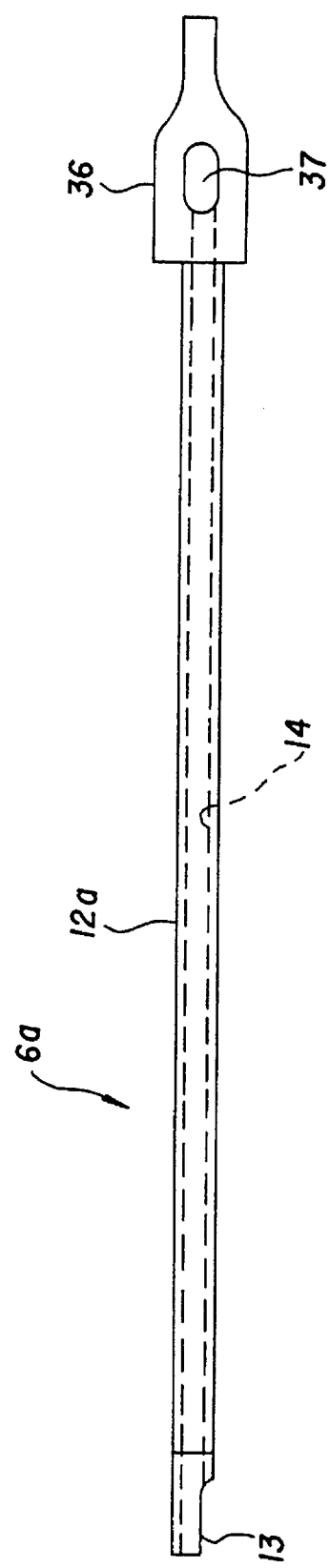

FIGS. 47 and 48 relate to the third embodiment of the present invention.

FIG. 47 is an explanatory view of an outer tube in which an inner tube is inserted.

FIG. 48 is a contour view of the inner tube.

DETAILED DESCRIPTION OF PREFERRED EMBODIMENTS

Embodiments of the present invention shall be concretely explained in the following with reference to the drawings.

A surgical resecting tool 1 is provided with a body and an insertable part 3 to be inserted into a body cavity. The above mentioned insertable part 3 comprises an outer tube 4 fixed in the opened base part to the tip part of the body 2 and an inner tube 6 rotatably inserted in this outer tube 4.

The above mentioned outer tube 4 is formed of an outer blade 8 made, for example, of a stainless steel and having a cutting port 7 opened on the outer periphery near the tip part and a pipe 11 made, for example, of a stainless steel, having this outer blade 8 fitted and fixed to the tip part and provided with a curved part 9 curved by an angle of 30 degrees so as to be easy to contact the above mentioned outer blade 8 with a living body tissue. The above mentioned inner tube 6 is provided with a flexible shaft 12 in which, for example, stainless steel wires are made three layers and the inner layer and outer layer are closely wound in the same direction but the intermediate layer is closely wound in the reverse direction so as to be able to transmit a torque and an inner blade made, for example, of a stainless steel, provided in the tip part of this flexible shaft 12 and loosely fitted within the above mentioned outer blade 8 and is curvably formed as in FIG. 3. On the other hand, an inner path formed within the inner tube 6 communicates with the above mentioned cutting port 7 and is a sucking path 14 sucking a cut piece of a living body tissue cut by the outer blade 8 and inner blade 13.

The inside diameter of the above mentioned curved part 9 is of a dimension larger than the outside diameter of the inner blade 13 so that the above mentioned inner blade 13 may pass. The outside or outer diameter of the inner tube 6 is smaller than the outside or outer diameter of the inner blade 13 as illustrated in FIGS. 1–3 of the drawings. The above mentioned body 2 is a part to be held by the hand of a surgeon or the like to operate the surgical resecting tool 1 and is formed of a housing 16 containing a driving part or the like rotating and driving the above mentioned inner tube 6 and a front housing 10 having a hollow 17 communicating with the sucking path 14 of the above mentioned outer tube 4 and fitted with a sucking tube mouthpiece 18 to be connected to a sucking and recovering apparatus 20. This front part housing 19 is removably screwed and connected to the housing 16, for example, by a screwing means, has an annular fixing part 21 extended forward and a groove 22 formed in the inner peripheral axial direction.

On the other hand, a sleeve 24 having a flange 23 forward is fitted on the outer periphery of the base part of the outer tube 4 and has a pin 26 erected on the outer periphery. The outer tube 4 fitted with the sleeve 24 with the above mentioned pin 26 engaged with the groove 22 is inserted in the base part into the fixing part 21 and an outer tube fixing screw body 27 is screwed on the outer periphery of the fixing part 21 to removably fix the outer tube 4 in the base part.

The above mentioned housing 16 is internally fitted in the rear part with a motor 28 as a driving part. A male spline 31 is fixed to a driving shaft 29 projected forward of this motor 28. On the other hand, in front of this motor 28, an output shaft 32 is rotatably and axially slidably borne and, in rear of the output shaft 32, a female spline 33 is formed to be meshed with the above mentioned male spline 31. In front of the above mentioned output shaft 32, a small diameter part 32a projecting into the hollow 17 of the above mentioned housing 16 is formed and further, in the front end part of this small diameter part 32a, a recess 32b opening forward as shown in FIG. 5 is provided. A projection 36a provided in the rear part of a sleeve 36 connected with the flexible shaft 12 at the rear end through a tubular connecting member 34 is to be engaged with this recess 32b so as to transmit the torque generated by the motor 28 to the flexible shaft 12. A window 37 communicating with the above mentioned sucking path 14 is provided on the outer peripheral surface of this sleeve 36 so that the cut living body tissue may be discharged into the sucking and recovering device 20 through the sucking path 14, window 37, hollow 17 and sucking tube mouthpiece 18.

The above mentioned sucking tube mouthpiece 18 is fitted as communicating with the hollow 17 of the above mentioned housing 16 and is inclined rearward with respect to the axial direction of the housing 16 so that the opening area of the inlet part may be taken to be large. The front housing 19 to which this sucking tube mouthpiece 18 is fitted is formed to be tapered to be smaller forward in the diameter so as to enlarge the opening area of the sucking tube mouthpiece 18.

Not only the outer tube 4 having the curved part 9 by 30 degrees shown in FIG. 2 but also the outer tubes 4 of the forms shown in FIG. 4 are prepared for the above mentioned outer tube 4. The outer tube 4a in FIG. 4 (a) is formed to be straight. The outer tube 4b in FIG. 4 (b) has the curved part 9 curved by 45 degrees and the cutting port 7 provided in the tip part is opened on the side reverse to the direction of the angle of 45 degrees. The outer tube 4c in FIG. 4 (c) has the curved part 9 curved by 90 degrees and the cutting port 7 provided in the tip part is opened on the side reverse to the direction of the angle of 90 degrees. The outer tube 4d in FIG. 4 (d) has the curved part 9 curved by 30 degrees and the cutting port 7 provided in the tip pat is opened in the direction of the angle of 30 degrees. The outer tube 4e in FIG. 4 (e) has the curved part 9 curved by 45 degrees and the cutting port 7 provided in the tip part is opened in the direction of the angle of 45 degrees.

Now, the operation of the surgical resecting tool 1 formed as mentioned above shall be explained.

Figure 6:
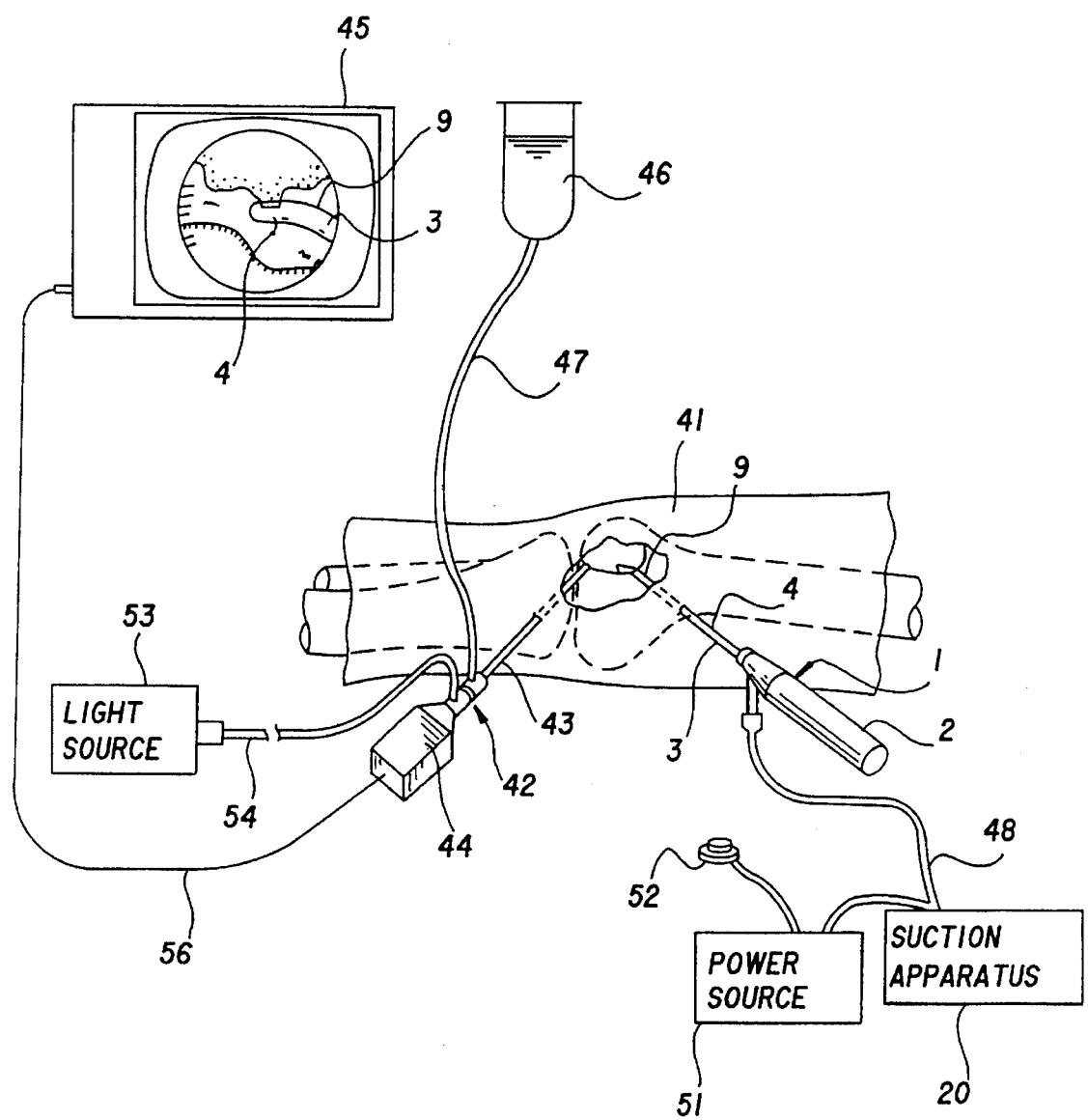

As shown in FIG. 6, in resecting such target part as, for example, an object tissue within a knee articulation, as a front step, the outer tube 4 having the most suitable curved part 9 is selected by the insertable part 3 piercing direction and the position of the part to be resected and the outer tube fixing screw body 27 of the body 2 is removed and replaced. The inner tube 6 to be inserted into this selected outer tube 4 is formed of the flexible shaft 12 and therefore can be curved and inserted in response to any curving angle. After this operation ends, the insertable part 3 of the surgical resecting tool 1 is inserted into a known part 41 through a trocar or the like provided by the piercing operation or directly.

By the way, before the above mentioned insertable part 3 is inserted, so that the object tissue may be resected while the articulation cavity interior is being observed, the insertable part of an articulatoscope 42 is inserted into the articulation cavity by a trocar or the like piercing operation and the articulation cavity interior and the insertable part 3 of the above mentioned surgical resecting tool 1 inserted into the above mentioned cavity are made observable directly from the eyepiece part of this articulatoscope 43 or in a displaying apparatus 45 displaying the video image photographed by a video camera fitted to the above mentioned eyepiece part. Further, so that the articulation cavity may be inflated to make the resecting operation easy, a physiological saline solution under a controlled hydraulic pressure is made feedable into the articulation cavity from a water feeding source 46 through a water feeding tube 47 pierced into the articulation cavity.

On the other hand, the sucking tube mouthpiece 18 provided in the front housing 19 of the surgical resecting tool 1 and the sucking and recovering device 20 are connected with each other through a tube 48 and a cable 49 is connected to an alternating current source 51 so that an electric power may be fed to the motor 28.

In such set state, while the articulation cavity interior and the tip side of the insertable part 3 of the resecting tool 1 are being observed by the operator with the articulatoscope 42 or the displaying apparatus 45, the cutting port 7 of the outer tube 4 is contacted with such tissue to be resected as a meniscus plate and, in this state, a foot switch 52 is switched on to drive the motor 28, rotate the inner tube 6 side inside the outer tube 4 and rotate the inner blade 13 fitted to the tip of the flexible shaft 12.

By the rotation of this inner blade 13, the tissue piece having come into the cutting port 7 can be resected.

The thus resected tissue piece will pass through the tube 48 through the sucking path 14 and will be recovered in the sucking and recovering apparatus.

In FIG. 6, the reference numeral 53 represents a light source apparatus, 54 represents a light guide cable and 56 represents a cable of a television camera.

As in this embodiment, in the case of resecting the object tissue within the articulation cavity, with the surgical resecting tool 1 having the straight outer tube 4, the inserting direction will be obstructed by such hard tissue as a bone and the object tissue will not be able to be reached in some case. However, in case there is such part hard to resect, when the outer tube 4 is replaced with the outer tube 4 having the most suitable curved part, the object part will be able to be easily resected.

By the way, the outer tube 4 is not limited to be of those forms in the above mentioned embodiment but may be insertable through the inner tube 6.

Figure 7:
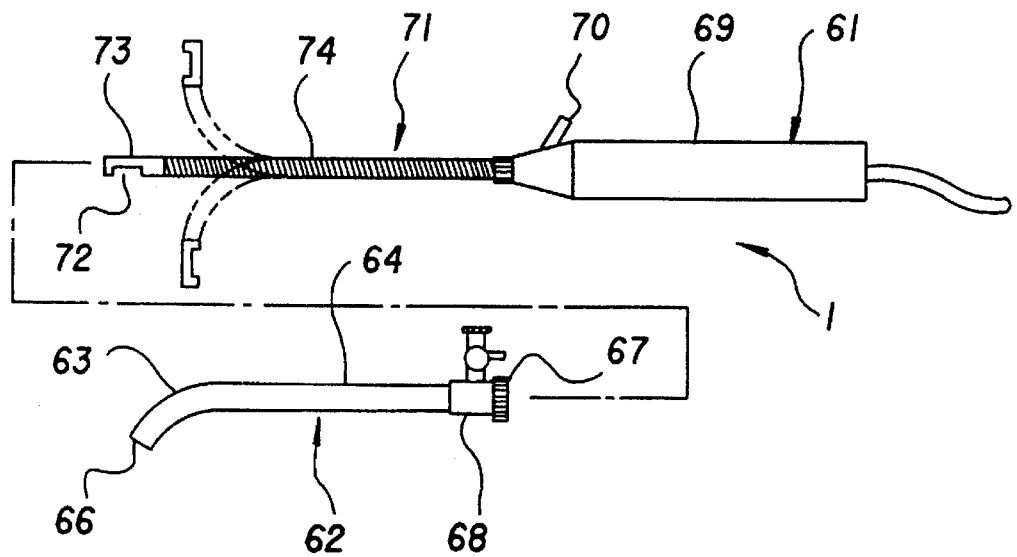
FIG. 7 to 9 relate to the second embodiment of the present invention.
Figure 8:
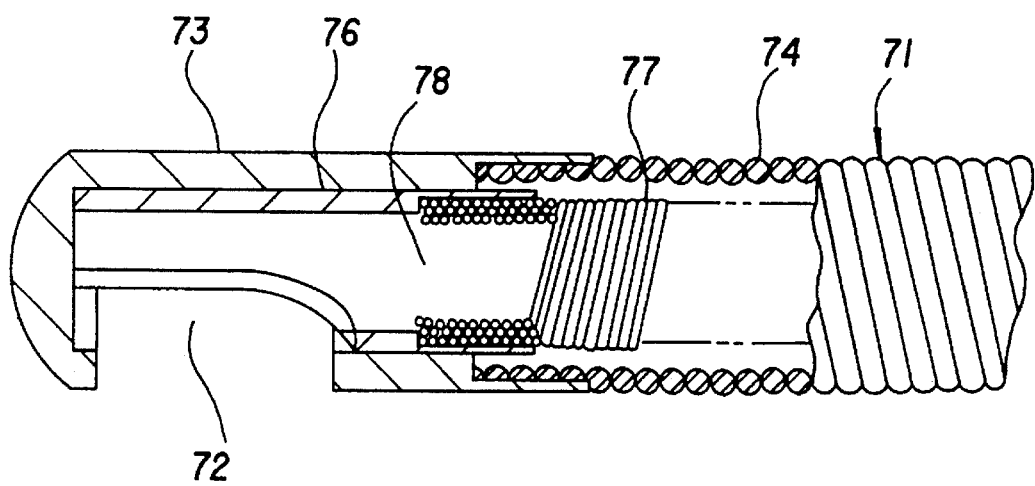
Figure 9A:
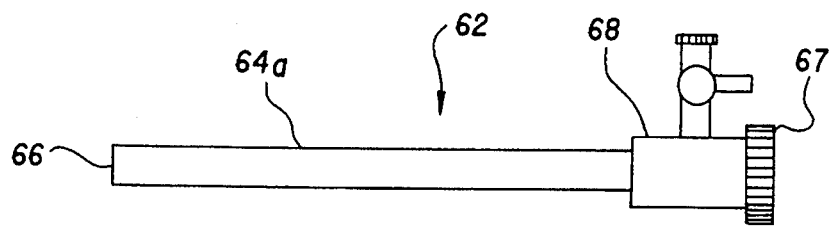
Figure 9B:
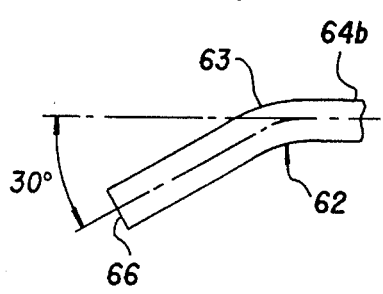
Figure 9C:
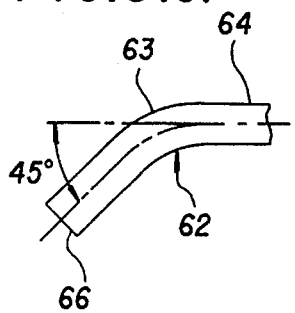
Figure 9D:
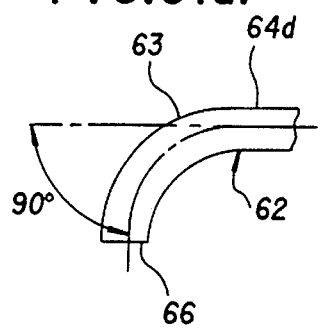

FIGS. 7 to 9 show the second embodiment of the present invention.

In this embodiment, the opening provided to open in the diametral direction in the first embodiment is provided to open forward.

The surgical resecting tool 1 is formed of a body 61 and an insertable part 62 to be inserted into a body cavity. The above mentioned insertable part 62 is formed of an outer tube 64 opening forward and having a curved part 63 near the tip part and a holding part 68 provided in the base part of this outer tube 64 and having an opening 67 communicating with an inserting path 66 formed within this outer tube 64.

The above mentioned body 61 is formed of a housing 69 containing a motor or the like and provided with a sucking tube mouthpiece 70 and an inner tube 71 extended forward. This inner tube 71 is formed of an outer blade 73 made, for example, of a stainless steel and having a cutting port 72 opened on the outer periphery near the tip part and a coil 74 having this outer blade 73 fitted and fixed to the tip part and curvably formed, for example, of a stainless steel wire.

Within the above mentioned outer blade 73, a tubular inner blade 76 made, for example, of a stainless steel is provided so as to be able to cut together with the above mentioned outer blade 73. A flexible shaft 77 wherein, for example, stainless steel wires are provided in three layers, with the inner layer and outer layer being respectively closely wound in the same direction and the intermediate layer is closely wound in the reverse direction so as to be able to transmit a torque, is inserted through the above mentioned coil 74 and is fitted and fixed to the rear end part of this inner blade 76. The outside or outer diameter of the flexible shaft 77 is smaller than the outside or outer diameter of the inner blade 76 as shown by FIG. 8 of the drawings. The inner path formed within the flexible shaft 77 communicates with the above mentioned cutting port 72 and is a sucking path 78 sucking a cut piece of a living body tissue so that the cut piece sucked from the above mentioned sucking tube mouthpiece 70 may be discharged.

By the way, in case the inner tube 71 is inserted into the insertable part 62, the outer blade 73 provided in the tip part of the inner tube 71 will project out of the insertable part 66 and will be able to contact and cut the part to be resected.

Such forms as are shown in FIG. 9 are prepared for the above mentioned outer tube 64. The outer tube 64a in FIG. 9 (*a*) is formed to be straight. The outer tube 64b in FIG. (b) has the curved part 63. The outer tube 64c in FIG. 9 (*c*) has the curved part 63 curved by 45 degrees. The outer tube 64d in FIG. (d) has the curved part 63 curved by 90 degrees.

Now, in inserting the surgical resecting tool 1 into the articulation cavity, first the outer tube 64 is inserted and then the inner tube 71 is inserted through the opening 67 with this outer tube 64 as a guide. The inner tube 71 is formed of the coil 74 and flexible shaft 77, is therefore curvable and can be easily inserted into even the outer tube 64 having the curved part 63. In some cases, depending on the curving angle of the outer tube 64, the part 60 to be resected will not be able to be reached. However, by replacing the outer tube with the outer tube 64 having a proper curving angle, the part to be resected can be reached and resected.

The other formations, operations and effects are the same as in the first embodiment.

Figure 10:
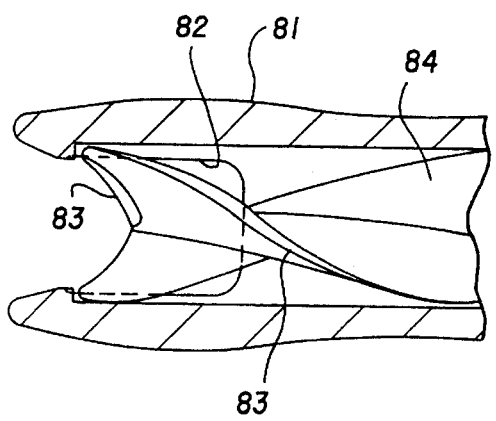
FIG. 10 is an explanatory view of the formation of an insertable tip which is a modification of the second embodiment.

FIG. 10 is an explanatory view of the formation of an insertable part tip which is a modification of the second embodiment.

An outer blade 82 is formed in the axial direction in the tip part of a cutting part 81 opening forward. Within this cutting part 81, an inner blade 84 formed to be spiral and provided with blade parts 83 on the outer peripheral surface and tip surface is rotably provided by a flexible shaft not illustrated. By such formation, the part to be resected in the axial direction and diametral direction can be cut.

Figure 11:
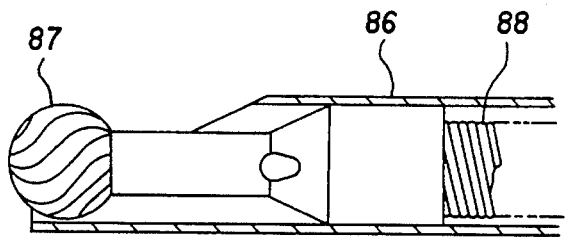
FIG. 11 is an explanatory view of the formation of an insertable part tip which is another modification of the second embodiment.

FIG. 11 is an explanatory view of the formation of an insertable part tip which is another modification of the second embodiment.

A spherical inner blade 87 having cutting blades formed on the outer peripheral surface is provided within a pipe 86 opening forward and made, for example, of a stainless steel. A flexible shaft 88 is rotatably connected to the rear end part of this inner blade 87. With such formation, the outer blade will be unnecessary and the formation will be simple.

The flexible shaft in the above mentioned respective embodiments need not be closely wound coils in three layers and may be, for example, in two layers or one layer. Further, the shaft which can transmit a rotary driving force and is curvable may be, for example, a spiral tube made by closely winding narrow long plates made of a stainless steel, made by knitting up very fine stainless steel wires or made by embedding a metal coil within a tube of a plastic or the like.

Also, the material of the inner tube and outer tube is not limited to be a stainless steel (for example, SUS 420F) but may be any material effective as a blade.

Further, the outer tube is not limited to be a stainless steel pipe but may be of any plastically transformable rigid material, for example, as of a plastic tube. Further, in the formation of the outer tube, a flexible part may be provided near the tip part so that the outer tube may be curvable by any desired angle by the operation from the base side.

As explained above, according to the present invention, as the outer tube to be inserted directly into an articulation cavity or the like is rigid, it can be inserted positively to the object part and, further, when the outer tube is provided with a curved part and the inner tube to be inserted through the outer tube is provided with a flexible part, even in case there is such hard tissue as a bone, the insertability will be high, the resecting operation will be easy, the formation will be simple and the cost will be able to be low.

Further, as the inner blade can be easily pulled out of the outer tube, they can be well washed and the resecting tool can be kept clean.

Figure 12:
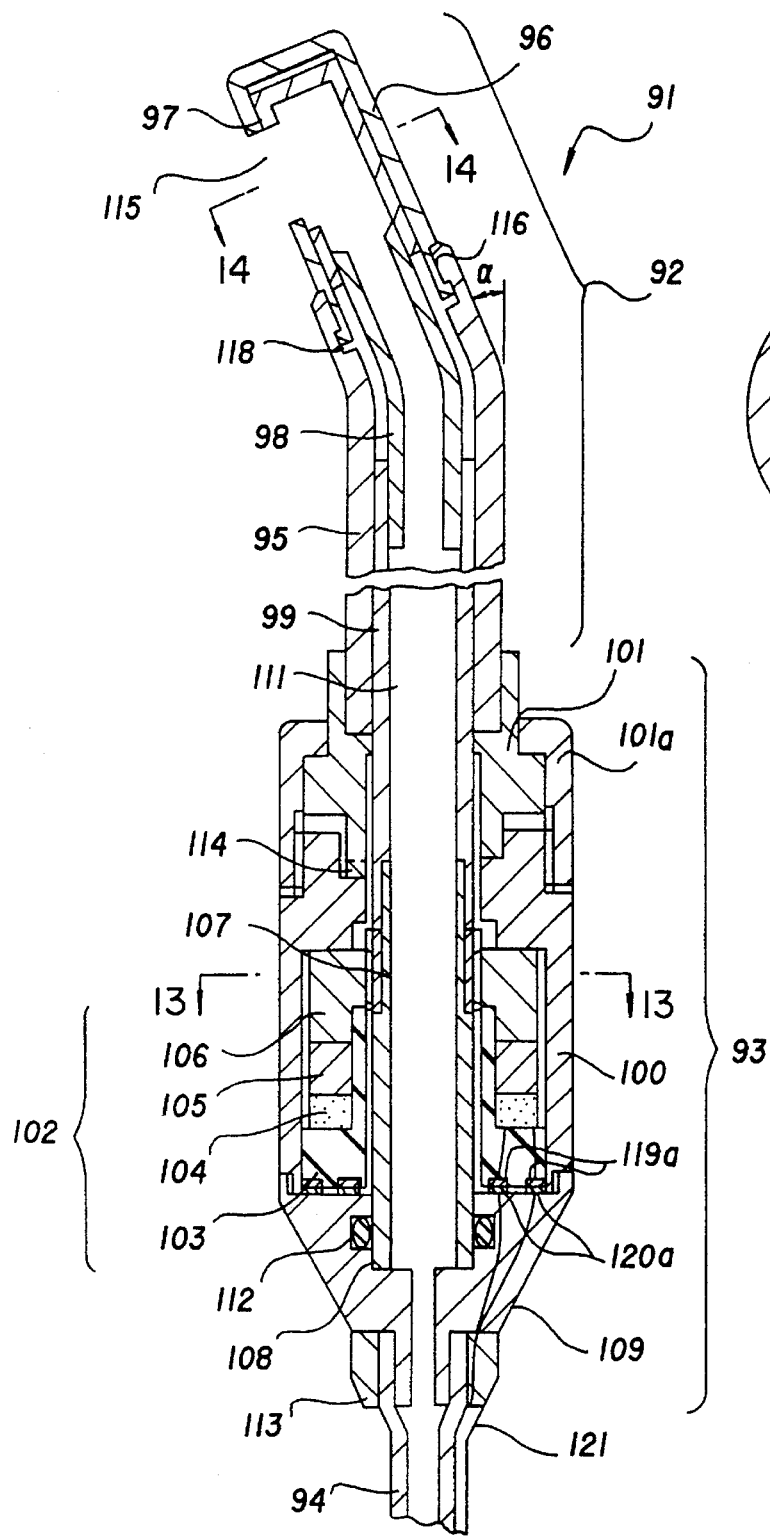

By the way, by varying the position of the cutting port, any desired resecting direction may be selected as shown in FIGS. 12 and 15.

Figure 13:
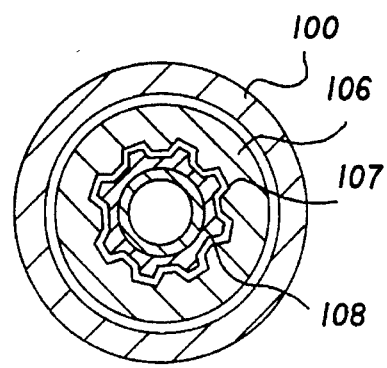
Figure 14:
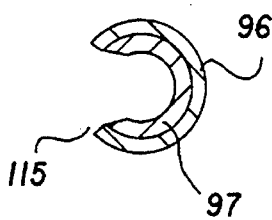

FIGS. 12 and 15 relate to a surgical resecting tool in which the cutting port can be rotated. FIG. 12 shows in the vertical section the structure of the surgical resecting tool. FIG. 13 is a sectioned view in the direction of the arrows 13—13 of FIG. 12. FIG. 14 is a sectioned view in the direction of the arrows 14—14 of FIG. 14. FIG. 15 shows the form of a movable outer tube.

As shown in FIG. 12, a surgical resecting tool 91 is formed of an insertable part 92 of a small diameter, an operating part 93 connected to the rear end of this insertable part 92 and a tube 94 extended out of the rear end part of this operating part.

The above mentioned insertable part 92 is coated with a rigid outer tube 95 and a movable outer tube 96 fitted to the tip of this outer tube 95. An inner blade 97 to be rotated and driven is contained inside this movable outer tube 96 and is fitted by soldering or brazing to the tip of a flexible inner tube 98 which is secured by soldering or brazing on the base (rear end) side to a rigid inner tube 99. The outside diameter of this inner tube 99 is made slightly smaller than the inside diameter of the outer tube 95 so that the inner tube 99 may be rotatable within the outer tube 95.

The above mentioned outer tube 95 is fitted on the base side into the front end side of an outer tube fixing member 101 fitted into the front end side of a cylindrical body cover 100 and is secured by soldering or brazing in this fitting part. This outer tube fixing member 101 can be removably fitted by a fixing ring 101 provided with a screw part screwed with a screw part on the outer periphery at the front end of the body cover 100.

An ultrasonic motor unit 102 rotating and driving the above mentioned inner tube 99 is arranged inside the above mentioned body cover 100.

This ultrasonic motor unit 102 is formed of an insulative supporting frame 103 fixed to the outside body cover 100, an annular piezoelectric body 104 fitted to the outer peripheral part of a small diameter of the cylinder of this supporting frame 103 by incising the outer periphery of the cylinder, an annular stator vibrator 105 fitted to the outer peripheral part made smaller in the diameter of the above mentioned supporting frame 103 while in contact with this piezoelectric body 104 and a rotor part 106 contacting, rotating and driving this stator vibrator 105.

As shown in FIG. 13, the above mentioned rotor part 106 is provided on the inner peripheral surface with a teeth to be engaged with an engaging gear 107. As this engaging gear 107 is secured to a rotary tube 108 inside it, the rotation of the above mentioned rotor part 106 will rotate and drive the rotary tube 108 through the engaging gear 107. This rotary tube 108 is secured by soldering or brazing to the inner tube 99 in front of the above mentioned engaging gear 107. Therefore, when the above mentioned rotary tube 108 is rotated, the inner tube 99 and flexible inner tube 98 will also be rotated and further the inner blade 97 will be rotated together with the flexible inner tube 98. By the way, as shown in FIG. 14, this inner blade 97 is fitted and rotatably contained in a movable outer tube part 96.

The above mentioned rotary tube 108 projects on the rear end side rearward from the body cover 100 and is fitted to the inner periphery of a rear lid 109 screwed to this body cover 100. This rear lid 109 is provided with a hollow which communicates with a hollow of the tube 94 fitted to the rear end of this rear lid 109 and with respective hollows of the flexible tube 98 to which the inner blade 97 is fixed on the base, inner tube 99 and rotary tube 108 and a sucking path 111 is formed of these hollows.

An O-ring 112 is contained in a peripheral groove formed on the inner peripheral surface of the above mentioned rear lid 109 so as to have a sealing function in contact with a rotary tube 108 to be rotated and driven.

The above mentioned tube 94 is fitted to the mouthpiece part of the rear lid 109 and is secured with a tube retainer 113.

The above mentioned outer tube 95 and inner tube 99 are removably fitted to the operating part 93. In this case, the outer tube 95 is secured to the outer tube fixing member 101 and the inner tube 99, engaging gear 107 and rotary tube 108 are made integral.

When the outer tube fixing member 101 is removed from the body cover 100 by disengaging the screwing with the fixing ring 101a, the outer tube 95 together with this outer tube fixing member 101 will be able to be removed from the operating part 93. When the inner tube 99 is pulled out, the inner tube 99 side can be removed from the operating part 93.

Therefore, as the tool 91 can be disassembled as described above, when it is used and washed, such tissue as is deposited within it will be easily removed.

The outer tube fixing member 101 is provided with a projection 114 for positioning coinciding with the bending direction of the outer tube 95. On the other hand, the body cover 100 is provided with a recess with which this projection 114 is to be engaged.

Now, in the first embodiment, the movable outer tube part 96 to be removably fitted to the tip of the outer tube 95 is of such structure as in shown in FIG. 15.

That is to say, the cylindrical movable outer tube part closed in the top part is provided on the side surface with an aperture 115 to be a resecting window so that a tissue piece having entered this aperture 115 may be resected with the (rotated and driven) inner blade 97 contained inside the aperture. This movable outer tube part 96 is incised to be like a step on the outer periphery on the base side except the flange part so as to form a thin wall part 116 and is provided with two slots in the part from the base side end to the tin wall part 116.

As the above mentioned movable outer tube part 96 is provided on the base side with the slots 117 so as to be resilient, when a force is applied to the flange part (base part) as indicated by the arrow C, this base side will be bent inward and will be able to be engaged by this bending with a peripheral groove 118 made on the inner peripheral surface near the tip of the outer tube 95. The inside diameter of this peripheral groove 118 is made slightly smaller than than the outside diameter of the above mentioned flange part so that the flange part side may be pressed into contact with this peripheral groove 118. When a torque is applied to this movable outer tube part 96 as thus pressed in contact against a friction force acting when it is pressed in contact, the movable outer tube part 96 fitting direction will be able to be freely changed with respect to the outer tube 95. That is to say, the direction of the aperture 115 will be freely changed.

The above mentioned piezoelectric body 104 is connected to ring-like contacts 119a (two contacts are shown in the illustration) through lead wires and is connected with a cable 121 extended outside the tube 94 through ring-like contacts 120a provided on the rear lid 109 side so as to contact these contacts 119a. This cable 121 is wound spirally, for example, on the tube 94 and is then connected to the piezoelectric body driving alternating current source 51 (See FIG. 6). Also, as shown in FIG. 6, the tube 94 communicating with the sucking path 111 is connected to the sucking and recovering device 20. Many electrodes on the non-earthing side of the above mentioned piezoelectric body 104 are provided radially and an alternating current voltage is applied to them from the alternating current source 51. In this case, when the many electrodes are piezoelectrically vibrated by sequentially applying an alternating current voltage displaced in the phase, the rings will be moved to rotate to one side and a rotor part 106 will be thereby rotated through the stator vibrator 105. The detailed explanation of this ultrasonic motor is mentioned, for example, in a Japanese patent application laid open No. 106126/1986.

By the way, in case outer tubes 95 which are different in the bending angle a on the tip side are prepared, the flexible inner tube 98 and inner blade 97 will be able to be used in common.

A foot switch 52 which can switch on and off the current source is extended out of the current source 51.

As the outer tube 95 is rigid as in the above mentioned FIGS. 12 to 15, in case it is to be introduced into a part to be resected, even if it contacts on the tip side with such hard part as a bone, its bending angle will not vary and therefore it will be easy to introduce it into the part to be resected. As the position of the aperture 115 can be freely set by rotating the movable outer tube part 96, the aperture 115 can be directed to be in any position in which the resection is easy and therefore the resection can be made simply.

Further, as shown in. FIG. 12, as the sucking path 111 is not bent within the operating part 93, the resected tissue will be able to be discharged without clogging the path. As the sucking path 111 is inserted through the center of the ultrasonic motor unit 102, the operating part will not be thick and the operation in case it is held by hand will be easy. As the sucking path 111 is not projected out of the side surface of the operating part 93 but is projected out of the rear end of it, in the case of the operation, the sucking path 111 will not be in the way and the operation will be easy.

The flexible inner tube 98 may be connected to the rotary tube 108 without using the inner tube 99.

Also, the movable outer tube part 122 may be formed as in FIG. 16. In FIG. 16, a movable outer tube 122 is provided with a projection 122a projecting slightly outward, for example, of the flange part of the movable outer tube part 96 in FIGS. 12 to 15 and the outer tube 95 is an outer tube 124 provided with holes 123a, 123b, - - - engaging with the above mentioned projection 122a in a plurality of places in the peripheral groove 11 part to be engaged with the above mentioned flange part. The others are the same as in FIGS. 12 to 15 mentioned above.

The same as in FIG. 15, the above mentioned movable outer tube 122 is made resilient by forming slots 117 on the base side and the inside diameter of the peripheral groove 11 is made slightly smaller than the outside diameter of the flange part so that the flange part contained within the peripheral groove 11 may be resilient to be expanded in the diameter. Therefore, in case the above mentioned projection 122a is engaged with the hole 123i (i=a, b, - - - ), a clicking function will act.

The setting angle position of this movable outer tube part 122 can be set in any position of a plurality of digital positions. The above mentioned movable outer tube parts 96 and 122 have no bent part and a bent part is provided near the tip of the outer tube 95. However, as in FIG. 17 and 1, an outer tube 131 is made a straight tube having no bent part but, on the other hand, a movable outer tube 132 is provided with a bent part 133 on the base side. The others are the same as in the above mentioned FIG. 12. Therefore, the same as in FIG. 12, the movable outer tube 132 can be set in any angle position so that, if it is rotated by substantially 180 degrees from the state, for example, in FIG. 17, it will be as in FIG. 18.

In such case, if movable outer tube parts 132 are different in the bending angle α are prepared, even the case of a different introducing direction will be able to be coped with.

In a surgical resecting tool 136 shown in FIGS. 19 and 20, for the projection 114 provided on the outer tube fixing member 101 as in FIG. 12, the body cover 100 is made a body cover 138 provided with not only a single positioning recess but also a plurality of recesses 137a, 137b, - - - as shown in FIG. 20.

Also, the movable outer tube part 96 and outer tube 95 are made integral to be such outer tube 139 as is shown in FIG. 19.

Therefore, when the projection 114 on the outer tube fixing member 101 side fitted with the outer tube 139 is engaged with any recess 137i (i=a, b, - - - ) among a plurality of recess 137a, 137b, - - - , as shown in FIG. 19, the direction of the bent tip side of the outer tube 139 will be able to be changed to any desired direction as shown in FIG. 19.

In FIGS. 19 and 20, an electric motor is contained inside a body cover 138 and is connected to a cable 140 projected out of the rear end of the body cover 138. A sucking mouthpiece 142 to be connected with a sucking tube 141 is provided on the side surface of this body cover 138.

In FIG. 21, another aperture 143 is provided in addition to the aperture 115 provided on the tip side of the outer tube 139 in FIG. 19 so as to be a plurality. In such formation, one of a plurality of the apertures 115 and 143 can be directed to the object part to be resected.

Further, even in case the direction in which one of the apertures 115 and 143 is to be set is not known, as there are a plurality of apertures, after they are actually inserted, if one of the plurality of apertures is pressed against the object position to be resected and the inner blade side is rotated, the tissue having entered the aperture in the pressed part will be able to be resected with the inner blade.

FIGS. 22 to 26 relate to a surgical resecting tool in which a cutting member provided at the tip of an inner tube is removably fitted.

In FIG. 22, a surgical resecting tool 146 is provided in the front part with an elongate insertable part 148 to be inserted into a body cavity, for example, an articulation cavity.

The above mentioned insertable part 148 is formed of an outer tube 149 fixed in the opened base to the tip part of a body 147 and an inner tube 150 rotatably internally fitted around a shaft within the outer tube 149. The outer tube 149 is made, for example, of a stainless steel and has in the illustrated example, a tissue taking blade port 151 opened at the tip and a fixed curved part 152 bending a blade port 151 at the tip by an angle, for example, of about 30 degrees so as to be easy to approach the tissue formed on the tip part side. On the other hand, the inner tube 150 comprises a closely wound coil and flexible synthetic resin tube (such as a multigoa tube or urethane tube) and has a cutting blade member 153 fixed at the tip. A communicating hole 153b communicating with the inner tube 150 from the cutting blade 153a side is formed in this cutting blade member 153. The tissue taking port 151 of the outer tube 149 communicates with the inner tube 150 through this communicating hole 153b. The inner path of this inner tube 150 is a cut piece sucking path 154 and is to be sucked by the sucking and recovering apparatus 20.

The tissue taking blade port 151 provided in the tip part of the above mentioned outer tube 149 is formed in the tip part of a tip forming member 155 removably fitted to the tip of the outer tube 149. This tip forming member 155 has an expanded diameter part 156 formed from the intermediate inner periphery to the rear end and has a female screw formed in the rear part of this expanded diameter part 156 and screwed with a male screw formed on the outer periphery made a little smaller in the diameter of the tip part of the outer tube 149 so as to be removably fitted to the tip part of the outer tube 149. On the other hand, the cutting blade member 153 at the tip of the inner tube 150 is removably fitted to the inner tube 150 and has on the outer periphery a flange 157 of an outside diameter engageable with the expanded diameter part 156 of the above mentioned tip forming member 155 so as to be engaged with and inserted into the expanded diameter part 156 of the tip forming member 155 and have the flange 157 contacted on the tip surface with a flange receiving shoulder or step 156a at the tip of the expanded diameter part 156. The inner tube 150 has an annular connector 158 fixed at the tip. After all, when the above mentioned tip forming member 155 is screwed and fixed to the outer tube 149, the cutting blade member 153 having the flange 157 engaged with and inserted into the expanded diameter part 156 of the above mentioned tip forming member 155 will have the flange 157 contacted on the tip surface with the step 156a of the expanded diameter part 156, will contact on the rear end surface with the connector 158 so as to be positioned and will have a key 153c formed at the rear end of the cutting blade member 153 fitted and fixed within the connector 158.

In the case of inserting and incorporating the inner tube 150 into the outer tube 149, while the cutting blade member 153 at the tip of the inner tube 150 is removed from the inner tube 150, the inner tube 150 is inserted into the outer tube 149 through the opening at the base. Then the cutting blade member 153 having the flange 157 engaged is inserted through the opening at the rear end into the expanded diameter part 156 of the tip forming member 155 removed from the outer tube 149. In this state, the tip forming member 155 is screwed and fixed to the outer tube 149 in the tip part so that the cutting member 153 will have the flange 157 contacted on the tip surface with the step 156a and on the rear end surface with the connector 158 of the inner tube 150 to have the front step positioned and the key 153c will be fitted and fixed in the connector 158 and will be incorporated into the tip part of the inner tube 150 to be able to transmit a torque of the inner tube 150.

In order to pull the inner tube 150 out of the outer tube 149 for washing or the like, first of all, the tip forming member 155 is removed from the tip part of the outer tube 149, the key 153c of the cutting blade member 153 is pulled out of the connector 158 of the inner tube 150 and the cutting blade member 153 is removed from the tip side of the outer tube 149. Then, the inner tube is pulled out of the base side opening of the outer tube 149.

Thus, so that the cutting blade member 153 at the tip of the inner tube 150 may be removably fitted from the tip side of the outer tube 149, a fixed curved part 152 is formed on the tip side of this outer tube 149. As the inner tube 150 can be easily internally fitted and incorporated and both inner tube 150 and outer tube 149 can be simply disassembled, they can be well washed. The cutting blade 153a is not restricted at all by the insertability of the inner tube 150 through the curved part of the outer tube 149 and therefore can be made larger. When the inner tube 150 is incorporated into the outer tube, the cutting blade member 153 will be able to be replaced. Further, as mentioned above, the insertable part 148 is bent in the tip part by an angle easy to approach the tissue by the presence of the curved part 152 and therefore the tissue taking blade port 151 at the tip is easy to approach the tissue.

With such formation as in FIGS. 27 and 28, the inner tube 150 may be kept clean. In FIGS. 27 and 28, tissue pieces and dirt are likely to clog the gaps of the respective coil material wires 150a of a closely wound coil forming the inner tube 150 and are difficult to wash and remove. Therefore, as shown in FIG. 27 the gaps between the respective coil material wires 150a are filled with such synthetic resin 150b as TEFLON or, as shown in FIG. 28, the material wires 150a of closely wound coils are embedded in a synthetic resin layer 150c.

In FIG. 29, the cutting blade member 153 and tip forming member 155 are molded of ceramics so that the wear of the cutting blade 153a and the reduction of the cutting efficiency may be prevented, the wear of the journal part 153d of the rotary cutting blade member 153 and the tip forming member 155 of the outer tube 149 bearing this journal part 153d may be prevented and the backlash by the wear may be eliminated. In the illustrated example, the key 153c in the rear part of the cutting blade member 153 is fitted directly into the tip of the inner tube 150 and the socket fixed in the inner tube is omitted.

In FIG. 30, a coil spring 161 for absorbing shocks is interposed between the connector 158 and cutting blade member 153 in FIG. 22. Therefore, the connector 158 is formed to be bottomed at the tip and the key 153c of the cutting member 153 is fitted into a key groove 162 formed on the bottomed tip surface of the connector 158. In such formation, the cutting blade member 153 can absorb shocks between it and the connector 158 of the inner tube 150.

In FIGS. 31 to 33, the cutting blade member 153 is removably fitted to the inner tube 150 by the attracting force of a magnet. A ring-like magnet 164 having an engaging key 163 is fixed to the rear part of the cutting blade member 153. On the other hand, a ring-like magnet 166 having an engaging recess 165 is fixed to the tip of the inner tube 150. Different poles are arranged on the opposed surfaces of both magnets 164 and 166 so that an attracting force may act. According to this formation, in removably fitting the cutting blade member 153 to the inner tube 150 from the tip side of the outer tuber 149, the tip part of the outer tube 149 is separated as a forming member and such step pressing the cutting blade part 153 is not required.

When the interior of the inner tube 150 is made a sucking path, the diameter of this path will have to be small and, when the above mentioned inner tube 150 is formed of a closely wound coil, cut pieces will clog the gaps of the coil material wires 150a. Therefore, for example, two cut piece sucking paths 167 are formed on the outer periphery of the outer tube 149 and are connected with the cutting blade member 153 part through communicating holes 168. A sealing member 169 is interposed between the cutting blade member 153 on the rear part side of the communicating holes 168 and the inner periphery of the outer tube 149.

In FIG. 36, an outer double tube part 170 elliptic in cross-section is formed on the outer peripheral side of the outer tube 149 and is closed in the short diameter part with the outer tube 149 and sucking paths 171 are formed on both arcuate side parts.

Figure 38:
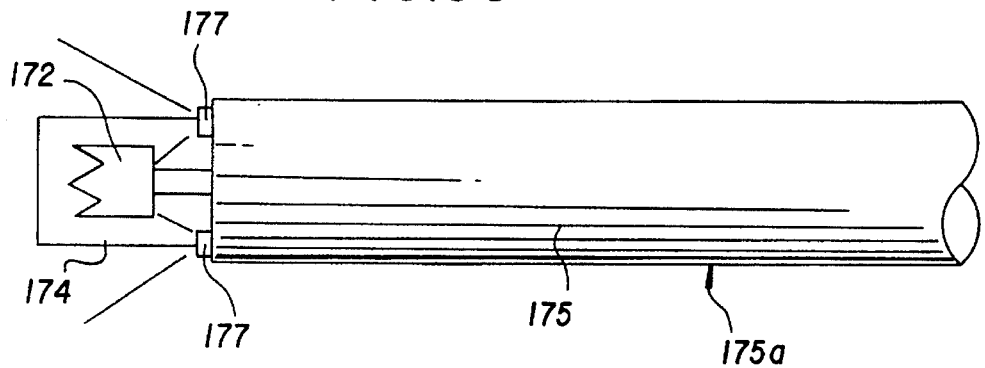

In FIGS. 37 and 38, a flexible shaft 173 rotating and driving a cutting blade 172 is incorporated into an outer tube 175 provided with an outer blade 174 at the tip to form an insertable part 175a of a surgical resecting tool. An observing means 176 and illuminating means 177 are arranged in the tip part of the above mentioned insertable part 175a so that a tissue may be resected while illuminating and observing the interior of a body cavity.

In the above mentioned observing means 176, a solid state imaging device 179 is arranged in the image forming position of objective lenses 178, an optical image is photo-electrically converted, is taken out as an electric signal by a signal cable 180 and is displayed in a displaying apparatus through a video processor or the like or an image guide consisting of an optical fiber bundle is arranged on the end surface in the image forming position of the objective lenses 178 and is extended to an eyepiece part. An image guide transmitting an illuminating light from an external light source, LED or lamp is used for the illuminating means 177.

In FIGS. 39 to 41, an outer tube is formed by assembling divided outer tube pieces on the outer periphery of an inner tube and then a form holding member is externally fitted from the base side of this outer tube to form an insertable part.

In FIG. 39, a surgical resecting tool 181 is provided in the front part with an elongate insertable part 182 to be inserted into a body cavity, for example, an articulation cavity.

The above mentioned insertable part 182 is formed of an outer tube 183 fixed in the opened base to the tip part of a body 181a and an inner tube 184 internally fitted rotatably around the axis within the outer tube 183. The outer tube 183 is made, for example, of a stainless steel or the like and, in the illustrated example, has a tissue taking blade port 185 opened at the tip and, on the other hand, a fixed curved part 186 bending by an angle, for example, of about 30 degrees formed on the tip side so as to have the blade port 185 at the tip easy to approach the tissue. Also, this outer tube 183 is formed to be dividable into a plurality, in the illustrated example, into two outer tube pieces 183a in the lengthwise direction. On the other hand, the inner tube 184 comprises a closely wound coil and flexible synthetic resin tube (such as a multigoa tube or urethane tube) and has a cutting blade member 187 fixed at the tip. A communicating hole 187b communicating with the interior of the inner tube 184 from the cutting blade 187a side is formed in this cutting blade member 187. The tissue taking blade port 185 of the outer tube 13 communicates with the interior of the inner tube 184. The inner path of this inner tube 184 is a cut piece sucking path 188 and is sucked by the sucking and recovering device.

The outer tube 183 made pipe-like by internally fitting the inner tube 184 and combining an outer tube piece 183a is externally fitted with a form holding member 189 pipe-like in the illustrated example so as to hold the contour of the outer tube 183. A screw hole 190 to the inner periphery is formed on the outer periphery on the base side of the form holding member 189 and an engaging recess 191 is formed on the outer periphery of the outer tube piece 183a to correspond to this screw hole 190 so that a fixing screw 192 may be screwed into the screw hole 190, may be engaged at the tip with the recess 191 of the outer tube piece 183a and may be fastened to fix the form holding member 189 to the outer tube 183. A flange 189a and fixing sleeve 189b are formed on the base side of this form holding member 189.

The fitting connecting part of the rear end part of the inner tube 184 having a flexibility with the sleeve 36 is coated on the outer periphery with a semi-rigid cover 193 so as to be reinforced. For this semi-rigid cover 193 is used a closely wound coil or thermocontracting Teflon tube.

In this formation, in combining the insertable part 182 with the body 181a, first of all, the outer tube pieces 183a divided in the lengthwise direction are combined to form the outer tube 183 on the outer periphery of the inner tube 174. In this state, the outer tube 183 is externally fitted from the base side with the form holding member 189, the screw hole 190 and the engaging recess 191 are made to coincide with each other and the fixing screw 192 is screwed into the screw hole 190, is engaged at the tip with the recess 191 and is fastened to fix the form holding member 189 to the outer tube 183 and to thereby form the insertable part 182. Then, this insertable part 182 is incorporated on the base side into the body 181a, the inner tube 184 is engaged with the output shaft 32 through the sleeve 36 and the fixing screw body 27 is screwed and fixed to the fixing part 21 of the front housing 19.

Thus, as the outer tube 183 is formed to be dividable in the axial direction, though the fixed curved part 186 is formed on the tip side of this outer tube 183, the inner tube 184 can be easily internally fitted and combined and the inner tube 184 and outer tube 183 can be easily disassembled to be well washed. Further, as the insertable part 182 is bent in the tip part by an angle easy to approach the tissue by the presence of the curved part 186 as mentioned above, the tissue taking blade port 185 at the tip is easy to approach the tissue.

The form and position of the cutting blade of the inner tube and the form and position of the tissue taking blade port of the outer tube are not limited to those in FIGS. 39 to 41 but can be variously set and formed.

Further, the position and curving angle of the fixed curved part of the outer tube can also be freely set. Therefore, if many outer tubes different in the curving angle are prepared, an outer tube of a curving angle easy to insert the insertable part into a body cavity and to approach the tissue to be resected can be selected to be used as combined with the inner tube and form holding member.

Further, in FIGS. 39 to 41, the inner tube is made flexible over all but may be flexible at least forward of the position corresponding to the curved part of the outer tube.

Further, the form holding member need not be pipe-like as in the embodiment but may be band-like to hold the outer tube with a plurality of band-like members.

In FIGS. 42 to 45, the inner tube is provided with a curving habit part.

In FIG. 42, a surgical resecting tool 196 is provided in the front part with an elongate insertable part 197 to be inserted into a body cavity, for example, an articulation cavity.

The above mentioned insertable part 197 comprises an outer tube 198 fixed in the opened base part 198a to the tip part of a body 196a and an inner tube 199 internally fitted within the outer tube 198 so as to be rotatable around the axis. The above mentioned outer tube 198 has a tissue taking blade port 200 opened on the side surface near the bottomed tip part. On the other hand, the inner tube 199 has a cutting blade port 201 opened in the position coinciding with the tissue taking blade port 200 of the outer tube 198 near the same bottomed tip part. The above mentioned outer tube 198 is connected and provided in the rigid base part 198a with a flexible tube 198b consisting of an elongate and, for example, closely wound coil (a multigoa tube or such synthetic resin tube as a urethane tube). This flexible tube 198b is connected and provided with a rigid tip forming member 198c having the above mentioned tissue taking blade port 200 formed at the tip. On the other hand, the inner tube 199 is formed of a flexible tube 199a consisting of a closely wound coil (multigoa tube or such synthetic resin tube as a urethane tube) having an outside diameter internally fitted by leaving a rotary clearance within the above mentioned flexible tube 198b and a cutting blade member 199b connected to the tip of this flexible tube 199a and provided with a cutting blade port 201.

In this embodiment, the above mentioned outer tube blade port 200 and inner tube blade port 201 will communicate with each other when they coincide with each other by the rotation of the inner tube 199, but will be closed when they are displaced from each other so that the tissue will be caught when both cutting ports 200 and 201 communicate with each other and will be resected and cut and the cut piece will be taken into the inner tube blade port 201 when both cutting ports are closed. The inner path of the above mentioned inner tube 199 is a cut piece sucking path 202 communicating with the outer tube blade port 200 and inner tube blade port 201 and communicates with the base side body 2 connecting the sucking and recovering apparatus 20.

A curving habit part 203 curving the blade ports 200 and 201 so as to be directed at a predetermined angle of inclination to the axial direction is formed, for example, on the tip part side in the insertable part 197 consisting of the above mentioned outer tube 198 and inner tube 199. By the way, the bending direction and angle of the blade ports 200 and 201 are not limited to those of the illustrated example but may be set in any direction and angle as required. The insertable part 197 having the above mentioned curving habit part 203 is to be used as inserted into and combined with a straight tubular guide pipe 204 and is formed to be of a length for which the curving habit part 203 can be inserted into or projected out of the tip. This guide pipe 204 is slidable in the axial direction with the insertable part 197 inserted through it and is internally fitted on the base side inner periphery with O-rings 205 in close contact with the outer periphery, for example, of the insertable part 197.

In such formation, the insertable part 197 consisting of the outer tube 198 and inner tube 199 and having the curving habit part 203 bending and directing the tip side cutting ports 200 and 201 in any predetermined direction of inclination is used as inserted in and combined with the straight tubular guide pipe 204 and, if the above mentioned curving habit part 203 is inserted and contained completely within the guide pipe 204, as shown in FIG. 45, the insertable part 197 will be able to be used as a straight tubular insertable part 197. If the curving habit part 203 is projected completely out of the tip opening of the guide pipe 204, the curved amount of the curving habit part 203 will be able to be adjusted by curving the curving habit part by a bending angle formed in advance and by adjusting the projected amount of the curving habit part 203 out of the tip opening of the guide pipe 204.

In FIG. 46, the flexible tube 199a of the inner tube 199 is made double to improve the following of the torque in case the rotary inner tube 198 is rotated in both normal and reverse directions. The inner and outer tubes are wound respectively in different directions so that, when the inside is wound, for example, clockwise, the outside will be wound counter-clockwise. In the illustrated example, the outer tube 198 is also of double coils but may be of a single coil. Further, the flexible tube of the inner tube is made of double tubes for clockwise and counter-clockwise rotations, the respective inner and outer tubes are formed of coils different respectively in the winding directions and, after all, the respective tubes may be quadruple.

In FIG. 42, the flexible tubes of the inner and outer tubes are formed of closely wound coils but flexible synthetic resin tubes may be used in place of them and only the curving habit parts of the inner and outer tubes may be made flexible and the others may be formed to be rigid members.

By the way, the forms and positions of the cutting ports of the outer tube and inner tube are not limited to those in the illustrated example but may be variously formed as required.

FIGS. 47 and 48 relate to the third embodiment of the present invention. FIG. 47 is an explanatory view of an outer tube in which an inner tube is inserted. FIG. 48 is a contour view of the inner tube.

In this embodiment, an inner tube 6a shown in FIGS. 47 and 48 is added to the formation of the first embodiment. By the way, an outer tube 4a shown in FIG. 47 is of the general explanatory view of the outer tube 4a shown in FIG. 4(a). The same component members as in the first embodiment shall bear the same reference numerals and shall not be explained here.

In this embodiment, the inner tube 6a shown in FIG. 48 can be connected further to the body 2 to which the inner tube 6 shown in the first embodiment can be removably connected. The inner tube 6a is to be inserted through the outer tube 4a as shown in FIG. 47.

The above mentioned outer tube 4a is made of a rigid pipe 11a formed linearly, for example, of stainless steel. The rigid pipe 11a is fitted at the base end with the sleeve 24 having the flange 23 described in the first embodiment and has an outer blade 8 made, for example, of stainless steel and having a cutting port opened on the outer periphery near the tip fixed to the tip.

The inner tube 6a inserted through the outer tube 4a is made of a rigid pipe 12a formed linearly, for example, of stainless steel. The rigid pipe 12a is provided at the tip with an inner blade 13 made, for example, of stainless steel so as to cut a living body tissue together with the above mentioned outer blade 8. Also, the rigid pipe 12a is provided at the base end with sleeve 36 described in the first embodiment so that a torque may be transmitted from the motor 28 within the body 2. By the way, the sleeve 36 is provided with a window part 37 communicating with the suction path 14 for discharging out of the body the living body tissue cut by the inner blade 13 provided within the inner tube 6a and the outer blade 8.

The other formations are the same as in the first embodiment.

In this embodiment, in the case of resecting an object tissue within an articulation cavity, when the object tissue can not be reached with the linear outer tube 4a as the inserting direction is obstructed by such hard tissue as a bone, the inner tube 6 provided with the flexible shaft 12 shown in the first embodiment will be connected to the output shaft 32 and the curved outer tube 4 most suited to resect the object tissue will be selected from among the outer tubes 4b, 4c, 4d and 4e shown in FIGS. 4(b) to (e) and will be connected to the body 2 so that the flexible shaft 12 of the inner tube 6 will be curved. Thus, by using the outer tube 4b, 4c, 4d or 4e, the object tissue which can not be reached with the linear outer tube 4a can be resected.

In case there is no such hard tissue obstructing the inserting direction as a bone, the linear inner tube 6a shown in FIG. 48 will be connected to the output shaft 32 and the linear outer tube 4a will be connected to the body 2.

By the way, in the first embodiment, the inner tube 6 provided with the flexible shaft 12 is inserted through the linear outer tube 4a to resect a living body tissue. However, the flexible shaft 12 is a metal wire wound like a coil and is somewhat lower in the torque transmitting efficiency. Therefore, in case the outer tube 4a is used and the inner tube 6a is not required to be curved, the linear inner tube 6a shown in FIG. 48 will be used to be able to improve the torque transmitting efficiency and to well resect the living body tissue.

By the way, the outer tube 4 and inner tube 6 are not limited to be of the forms shown in FIGS. 47 and 48 but the outer blade 82 and inner blade 84 or 87 of the forms shown in FIGS. 10 ad 11 may be provided. Thus, when a plurality of kinds of outer tubes and inner tubes are prepared, the outer tube and inner tube conforming to a living body tissue to be resected will be able to be used and the efficiency of the resecting operation will be able to be improved.

The other operations and effects are the same as in the first embodiment.

What is claimed is:

1. A surgical resecting tool for insertion into an articulation cavity or the like to resect an affected part with a torque, comprising:

a body part provided with a handle and having a rotating power source;

an outer tube having a rear part removably fitted to said body part, said outer tube having an aperture opening in a front part thereof, said outer tube having a bent part bending at a predetermined angle in the rear of said aperture opening;

an inner tube inserted into said outer tube so that said inner tube can be rotated on an axis, a rear end of said inner tube removably joined to the rotating power source of said body part so as to be rotated and driven thereby, said inner tube having at least a portion being flexible with the flexible portion of said inner tube located internally of the bent part of said outer tube;

a connector fixed to a distal end of said inner tube;

a cutting part located in the front part of said outer tube provided with said aperture opening;

a key provided to one of a rear end of said cutting part and said connector;

a key groove provided to the other one of said rear end of said cutting part and said connector, and said key is fitted into said key groove to removably connect said cutting part to said distal end of said inner tube to transmit the rotation of said inner tube to said cutting part.

2. A surgical resecting tool according to claim 1, wherein said cutting part has a flange, a radially extending flange receiving shoulder extends around an inner periphery of said outer tube, said flange receiving shoulder is located at a predetermined distance relative to said aperture opening and said distal end of said inner tube, and said flange is fitted to said flange receiving shoulder.

3. A surgical resecting tool according to claim 2, wherein said front part of said outer tube is comprised of a tubular tip forming member removably fitted to said outer tube and said flange receiving shoulder is provided on an inner periphery of said tip forming member.

4. A surgical resecting tool according to claim 1, wherein said cutting part is a molded ceramic cutting part, said front part of said outer tube is a molded ceramic tubular tip forming member removably fitted to said outer tube, and said cutting part is journalled on an internal surface of said tubular tip forming member.

5. A surgical resecting tool according to claim 2, including means provided between said cutting part and said connector for biasing said cutting part into engagement with said flange receiving shoulder and absorbing shocks between said cutting part and said connector.

6. A surgical resecting tool according to claim 5, wherein said means biasing said cutting part into engagement with said flange receiving shoulder is a coil spring.

7. A surgical resecting tool according to claim 1, wherein said cutting part and said distal end of said inner tube are removably connected by at least one magnet.

8. A surgical resecting tool according to claim 1, wherein said cutting part and said distal end of said inner tube are removably connected by a pair of magnets with each magnet having a different polarity relative to the polarity of the other magnet and wherein one of said magnets comprises said connector.

9. A surgical resecting tool according to claim 8, wherein said one of said magnets is a ring-shaped magnet having said key groove and the other of said magnets provides said key and is fixed to a rear part of said cutting part.

10. A surgical resecting tool according to claim 1, wherein said key is provided at said rear end of said cutting part and said key groove is provided to said connector.

* * * * *